US006495498B2

(12) United States Patent
Niemiec et al.

(10) Patent No.: US 6,495,498 B2
(45) Date of Patent: *Dec. 17, 2002

(54) DETERGENT COMPOSITIONS WITH ENHANCED DEPOSITING, CONDITIONING AND SOFTNESS CAPABILITIES

(75) Inventors: Susan M. Niemiec, Yardley, PA (US); Hsing Yeh, Hillsborough, NJ (US); Regina Gallagher, Cranbury, NJ (US)

(73) Assignee: Johnson & Johnson Consumer Companies, Inc., Skillman, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/321,074

(22) Filed: May 27, 1999

(65) Prior Publication Data

US 2002/0077256 A1 Jun. 20, 2002

(51) Int. Cl.$^7$ .......................... A61K 7/075; C11D 1/02; C11D 3/37
(52) U.S. Cl. .................. 510/122; 510/119; 510/121; 510/123; 510/129; 510/466; 424/401; 424/70.12; 424/70.19
(58) Field of Search ................ 510/119, 121, 510/122, 123, 129, 466; 424/401, 70.12, 70.19

(56) References Cited

U.S. PATENT DOCUMENTS

| 4,292,212 A | 9/1981 | Melby ........................ 252/547 |
| 4,472,297 A | 9/1984 | Bolich, Jr. et al. .......... 252/531 |
| 4,704,272 A | 11/1987 | Oh et al. ....................... 424/70 |
| 4,741,855 A | 5/1988 | Grote et al. ................. 252/142 |
| 5,098,979 A | 3/1992 | O'Lenick, Jr. ............... 528/15 |
| 5,221,530 A | 6/1993 | Janchitraponvej et al. .... 424/70 |
| 5,244,664 A | 9/1993 | Godtfredsen ................. 424/401 |
| RE34,584 E | 4/1994 | Grote et al. ................. 252/142 |
| 5,344,643 A | * 9/1994 | Thiel et al. .................... 424/70 |
| 5,417,965 A | 5/1995 | Janchitraponvej et al. . 424/70.12 |
| 5,776,443 A | * 7/1998 | Vinski et al. ............. 424/70.12 |
| 5,977,036 A | * 11/1999 | Guskey ....................... 510/121 |
| 5,989,533 A | * 11/1999 | Deegan et al. ........... 424/70.28 |
| 6,106,815 A | * 8/2000 | Kang et al. .............. 424/70.12 |
| 6,274,130 B1 | 8/2001 | Murray ..................... 424/70.12 |

FOREIGN PATENT DOCUMENTS

| DE | 4330 597 A1 | 3/1995 |
| EP | 45720 B | 2/1982 |
| EP | 80976 B | 6/1983 |
| EP | 0 047 714 B1 | 10/1985 |
| EP | 0 018 717 B2 | 1/1991 |
| EP | 0 155 806 | 1/1991 |
| EP | 0511 652 B | 4/1992 |
| EP | 0 521 666 B1 | 1/1993 |

(List continued on next page.)

OTHER PUBLICATIONS

Beylot, C., et al., "Oral contraceptives and cyproterone acetate in female acme treatment," *Dermatology*, 1998, 196, 148–152 No Month Given.

(List continued on next page.)

*Primary Examiner*—Mark Kopec
*Assistant Examiner*—Brian P. Mruk
(74) *Attorney, Agent, or Firm*—Erin M. Hammon

(57) ABSTRACT

Novel "two-in-one" detergent compositions comprised of at least one water soluble silicone agent, at least one cationic conditioning agent, and a detergent. These compositions are suitable for use in shampoos, baths, and shower gels. Also described is a novel delivery system for depositing benefit agents into and onto the skin, nails, and/or hair comprised of at least one water soluble silicone and at least one cationic conditioning agent.

24 Claims, 1 Drawing Sheet

20 μm

FOREIGN PATENT DOCUMENTS

| | | | |
|---|---|---|---|
| EP | 0 522 756 B1 | 1/1993 | |
| EP | 0 465 734 B1 | 3/1994 | |
| EP | 0 601 163 B1 | 6/1994 | |
| EP | 0 617 953 B1 | 11/1994 | |
| EP | 0 648 105 B1 | 4/1995 | |
| EP | 0 659 404 A2 | 6/1995 | |
| EP | 0 659 404 A3 | 6/1995 | |
| EP | 0 562 263 B1 | 10/1995 | |
| EP | 0 697 208 B1 | 2/1996 | |
| EP | 0 756 859 B1 | 2/1997 | |
| EP | WO 97/26860 * | 7/1997 | |
| EP | WO 92/29094 * | 7/1998 | A61K/7/50 |
| EP | WO 98/29094 * | 7/1998 | |
| GB | 2 057 261 B1 | 4/1981 | |
| GB | 2161172 A | 1/1986 | |
| GB | 2281913 A | 3/1995 | |
| JP | 7-2677 | 6/1995 | |
| WO | WO 93/11737 | 6/1993 | |
| WO | WO 94/18934 | 9/1994 | |
| WO | WO 97/47274 | 2/1997 | |
| WO | WO 97/26860 | 7/1997 | |
| WO | WO 97/38672 | 10/1997 | |

OTHER PUBLICATIONS

Gollnick, H., et al., "Topical drug treatment in acne," *Dermatology*, 1998, 196, 119–125 No Month Given.

Meynadier, J., et al., "Systemic antibotics for acne," *Dermatology*, 1998, 196, 135–139 No Month Given.

Orfanos, C.E., et al., "Oral retinoids in the treatment of seborrhea and acne," *Dermatology*, 1998, 196, 140–197 No Month Given.

Piéard, G.E., et al., "New insight into the topical management of excessive sebum flow at the skin surface," *Dermatology*, 1998, 196, 126–129 No Month Given.

Schmidt, J.B., "Other antiandrogens," *Dermatology*, 1998, 196, 153–157 No Month Given.

Toyoda, M., et al., "An overview of topical antibotics for acne treatment," *Dermatology*, 1998, 196, 130–134 No Month Given.

Weigmann, et al., "Principles of polymer science and technology in cosmetics and personal care," *Cosmetic Science and Technology Series*, Goddard, E.D., et al., (Eds.), 1999, 22, 554–569 No Month Given.

English Abstract (DE 4330597A1) 1995.

Topical Drug Treatment in Acne, Dermatology 1998: 196:119–125, Gollnick, Schramm No Month Given.

Secondary Ion Mass Spectrometry pp 185–193, A Guide to Materials Characterization and Chemical Analysis by John P. Sibilia 1988, VCH Publishers, Inc. No Month Given.

Angular Dependent X–Ray Photoelectron Spectroscopy pp 196–197, A Guide to Materials Characterization and Chemical Analysis by John P. Sibilia, 1988, VCH Publishers, Inc. No Month Given.

Apparatus for Radial Compression of a Hair Tress, pp 554–556, Weigmann and Kamath, Hair and Hari Care in Cosmetic Science and Technology Series, vol. 17, Editor Dale H. Johnson, 1997, Marcel Dekker, Inc. No Month Given.

Measurement of Bulk Compressibility, Garcia, et al. Synopsis [presented at $10^{th}$ IFTSCC Congress, Sydney, Australia (1978)] No Month Given.

* cited by examiner

20 μm

15 μm

US 6,495,498 B2

DETERGENT COMPOSITIONS WITH ENHANCED DEPOSITING, CONDITIONING AND SOFTNESS CAPABILITIES

BACKGROUND OF THE INVENTION

1. Field of Invention

This present invention relates to detergent compositions that not only effectively cleanse the hair but also impart superior wet stage and dry stage conditioning properties to the hair in a single application. The present invention is further directed to a novel delivery system for delivering benefit agents onto and/or into the surface of the skin, nails, and/or hair, and methods of using such systems.

2. Background of the Invention and Prior Art

Consumers often desire to have a hair shampoo that not only effectively cleanses the hair, but that also imparts other desirable properties, such as conditioning and lathering, to the hair. Because nonionic, amphoteric and zwitterionic surfactants are relatively inferior cleansing surfactants in comparison to anionic surfactants, hair shampoos generally are formulated with the latter, which thoroughly cleanses as opposed to conditions the hair. Hence, hair that has been shampooed with an anionic surfactant-based composition usually appears unconditioned and is considered to be cosmetically unappealing. Furthermore, anionic surfactants adversely leave the hair with an undesirable harsh and "dry to the touch" feel, which is difficult to comb in either the wet or dry state. Even after complete drying, such thoroughly cleansed hair remains unsatisfactory in hair softness and "flyaway" properties. Thus, it is usually necessary to perform a post-shampoo conditioning step to such hair in order to ameliorate these undesirable physical characterstics.

With the advent of so-called "two-in-one" conditioning shampoos, it became possible to condition and cleanse hair simultaneously. However, it is well known that the formulation of such "two-in-one" conditioning shampoos is difficult due to the inherent incompatiblity between the cleansing anionic surfactants and the cationic conditioning agents. Unfortunately, those known "two-in-one" conditioning shampoos that have overcome the incompatibility problem disadvantageously possess inferior cleansing and conditioning properties.

One known method for reducing the incompatibility between the anionic surfactants and the cationic conditioning agents is through the use of alternative, non-anionic surfactants and improved cationic conditioning agents. However, such alternative, non-anionic surfactants possess relatively inferior cleansing properties.

Other efforts have concentrated on varying the types of conditioners. Cationic conditioning agents disadvantageously do not generally provide optimal overall conditioning benefits, particularly in the areas of "softness" and "wet/dry combing", when delivered as an ingredient in a shampoo composition. Water-insoluble conditioning agents, such as the non-volatile silicones that are well recognized in the art as providing a degree of softness to the hair, often results in unstable "two-in-one" formulations. See U.S. Pat. Nos. 4,704,272; 4,741,855; and U.S. Pat. No. RE 34,584. Substantive cationic polymers, which are capable of depositing on the hair shaft during shampooing to impart the desired degree of manageability, disadvantageously result in formulations that give the hair a greasy feeling or "build-up" on hair. See U.S. Pat. Nos. 5,221,530; 5,417,965; 4,292,212; and 4,472,297.

Another important property of cleansing compositions that is desired by consumers is lathering. Consumers often associate high lathering with effective cleansing, and typically prefer high lathering shampoos to low lathering shampoos from an aesthetic standpoint. Unfortunately, many therapeutic shampoos, in particular those possessing therapeutic agents such as anti-dandruff agents, contain active agents that tend to adversely affect lathering performance. It is well known that the deposition of therapeutic agents on the hair or skin may be improved via significantly increasing the levels of therapeutic agents in the shampoo compositions. However, not only does the use of such high levels therapeutic agents disadvantageously increase raw materials costs, but also it also reduces the latherability of the shampoo and deleteriously affects product stability. The presence of detergents in the anti-dandruff shampoos also interferes with the ability of therapeutic agents to deposit onto the hair because the detergents are designed to carry or remove oil, grease, dirt, and particulate matter from the hair and scalp during rinsing.

Accordingly, it would be highly desirable to find a "two-in-one" cleansing composition capable of effectively cleansing and detangling the hair while imparting superior wet and dry combing and softness thereto, without creating "build-up". It would also be desirable to have a high-lathering "two-in-one" cleansing composition that not only effectively cleansed the hair but also deposited a significant amount of therapeutic agents onto the hair and skin.

SUMMARY OF THE INVENTION

In accordance with this invention, there is provided a cleansing composition comprising, consisting essentially of, and/or consisting of:
   a) at least one water soluble silicone agent;
   b) at least one cationic conditioning agent; and
   c) at least one detergent.

Another embodiment of the present invention is directed to a delivery system for delivering benefit agents into and/or onto the hair, nails, and scalp comprised of, consisting essentially of, and/or consisting of:
   a) at least one water soluble silicone agent; and
   b) at least one cationic conditioning agent.

Another embodiment of the present invention is directed to a method for enhancing the deposition of benefit agents which comprises, consists essentially of, and/or consists of topically administering to a human or animal a composition comprised of, consists essentially of, and/or consists of:
   a) a delivery system comprised of
     i) at least two cationic conditioning compounds selected from the group consists of guar hydroxypropyltrimonium chloride, acrylaminopropyltrimonium chloride/acrylamide copolymer, and mixtures thereof;
     ii) at least one water soluble silicone compound comprised of silicone quaternium-13; and
   b) an effective amount of a benefit agent to a desired location on the skin, hair, and/or nails.

Yet another embodiment is directed to a method for depositing a thin coating of conditioner on a hair fiber, comprised of, consisting essentially of, and/or consisting of:
   a) topically applying an effective amount of a delivery system composition comprised of
     i) at least two cationic conditioning compounds selected from the group consisting of guar hydroxypropyltrimonium chloride, acrylaminopropyltrimonium chloride/acrylamide copolymer, and mixtures thereof;
     ii) at least one water soluble silicone compound comprised of cetyl triethylmonium dimethicone copolyol phthalate; and
     iii) a hydrophilic benefit agent to a desired location on the hair of a human or animal.

Yet another embodiment is directed to a method for treating hair loss comprising, consisting essentially of, and/or consisting of topically administering to a human or animal at a desired area for treating hair loss a composition comprised of, consisting essentially of, and/or consisting of based upon the total weight of the composition:
- A. a delivery system comprised of
  - i) at least one water soluble silicone agent;
  - ii) at least one cationic conditioning agent; and
- B. an effective amount of a hair loss treatment agent.

Another embodiment is directed to a method for inhibiting hair growth comprising, consisting essentially of, and/or consisting of topically administering to a human or animal at a desired area for inhibiting hair growth a composition comprised of, consisting essentially of, and/or consisting of, based upon the total weight of the composition:
- A. a delivery system comprised of
  - i) at least one water soluble silicone agent;
  - ii) at least one cationic conditioning agent; and
- B. an effective amount of a hair growth inhibiting agent.

Another embodiment of the present invention is directed to a method for treating or minimizing the effects of aging comprising, consisting essentially of, and/or consisting of topically administering to a human or animal at a desired area a composition comprised of, consisting essentially of, and/or consisting of based upon the total weight of the composition:
- A. a delivery system comprised of
  - i) at least one water soluble silicone agent;
  - ii) at least one cationic conditioning agent; and
- B. an effective amount of an anti-aging active agent.

Another embodiment of the present invention is directed to a method for treating acne comprising, consisting essentially of, and/or consisting of topically administering to a human or animal at a desired area a composition comprised of, consisting essentially of, and/or consisting of, based upon the total weight of the composition:
- A. a delivery system comprised of
  - i) at least one water soluble silicone agent;
  - ii) at least one cationic conditioning agent; and
- B. an effective amount of an anti-acne active agent.

Another embodiment of the present invention is directed to a method for depigmenting skin comprising, consisting essentially of, and/or consisting of topically administering to a human or animal at a desired area a composition comprised of, consisting essentially of, and/or consisting of based upon the total weight of the composition:
- A. a delivery system comprised of
  - i) at least one water soluble silicone agent;
  - ii) at least one cationic conditioning agent; and
- B. an effective amount of a depigmentation active agent.

In yet another embodiment of the present invention is a method for treating the diseases of dandruff, seborrheic dermatitis, and psoriasis and/or the symptoms associated therewith comprising, consisting essentially of, and/or consisting of topically administering to a human or animal at a desired area a composition comprised of, consisting essentially of, and/or consisting of based upon the total weight of the composition:
- A. a delivery system comprised of
  - i) at least one water soluble silicone agent;
  - ii) at least one cationic conditioning agent; and
- B. an effective amount of a benefit agent selected from the group consisting of an anti-dandruff agent, an anti-seborrheic dermatitis agent, an anti-psoriasis agent, and mixtures thereof.

The composition of this invention, when used in a shampoo or body cleanser, possesses one or more of the following properties: lathering, cleansing, wet detangling, wet combining, dry combing, conditioning, softness, manageability, rinseabiity, and ability to significantly deposit therapeutic agents. Moreover, the delivery system of the present invention is capable of effectively depositing benefit agents into and/or onto the skin, hair and nails.

BRIEF DESCRIPTION OF THE DRAWINGS

The above and other aspects and novel features of the present invention will become apparent from the following detailed description of the preferred embodiments, as illustrated in the accompanying figures showing the improved hair conditioning properties imparted by using the method and composition of the present invention, wherein:

FIG. 1(*b*) is a mass spectrometric representation of a hair fiber previously treated with a cleansing composition of the present invention as described in Example 11.

DETAILED DESCRIPTION OF PREFERRED EMBODIMENTS

Figure 1A:
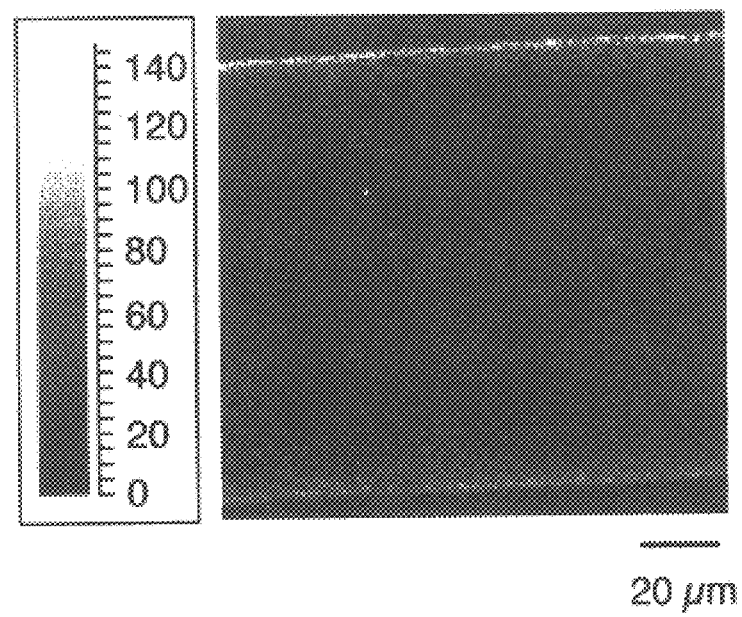
FIG. 1(*a*) is a mass spectrometric representation of a hair fiber previously treated with Pantene Pro-V shampoo.

In one embodiment of the present invention, the cleansing composition may suitably comprise, consist of, or consist essentially of: a) at least one water soluble silicone agent; b) at least one cationic conditioning agent; and c) at least one detergent. Preferably, the cleansing composition contains, based upon the total weight of the cleansing composition, a) from about 0.001 percent to about 20 percent, and preferably from about 0.01 percent to about 5 percent of water soluble silicone agents; b) from about 0.01 percent to about 10 percent, and preferably from about 0.1 percent to about 5 percent of cationic conditioning agents; and c) from about 0.01 percent to about 30 percent, and preferably from about 5 percent to about 20 percent detergent.

The first component of the cleansing composition is a water soluble or insoluble silicone agent, with water soluble silicone agents being preferred. Examples of suitable water soluble silicone agents nonexclusively include the water soluble dimethicones substituted with fatty acid moieties, water soluble silicone quaterniums, and mixtures thereof. Either volatile or nonvolatile water soluble silicones are suitable for use in the present invention, with the latter being preferred. Preferably, the water soluble dimethicones are substituted with fatty acid moieties selected from fatty acids having from about 5 carbon atoms to about 30 carbon atoms and the silicone quaterniums contain about 6 carbon atoms to about 20 carbon atoms.

Examples of suitable water soluble volatile silicone agents nonexclusively include polydimethylsiloxane, hexamethyldisiloxane, cyclomethicone fluids such as polydimethylcyclosiloxane available commercially from Dow Corning Corporation of Midland, Mich. under the tradename, "DC-345" and mixtures thereof, with the cyclomethicone fluids being preferred.

Examples of suitable water soluble nonvolatile silicone agents nonexclusively include cetyl triethylmonium dimethicone copolyol phthalate, stearalkonium dimethicone copolyol phthalate, dimethicone copolyol having the following structure I:

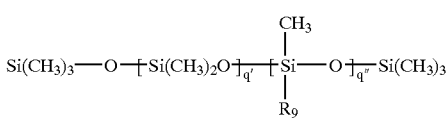
I.

Wherein:
q' is an integer from about 1 to about 7000;
q" is an integer from about 1 to about 5000;
$R_9$ may be any water soluble group such as:
  a) a fatty alcohol having from about 8 carbon atoms to about 30 carbon atoms;
  b) a fatty acid having from about 8 carbon atoms to about 30 carbon atoms, and derivatives thereof;
  c) a crosslinked water soluble polymer such as mercaptol propyl copolymer;
  d) a cationic moiety, e.g. trimonium chloride;
  e) propyl PG-Betaine;
  f) polypeptides such as polysarcosine, and
  e) mixtures thereof, dimethicone copolyol acetate, dimethicone copolyol lactate, dimethicone copolyol laurate, dimethicone copolyol methyl ether, dimethicone copolyol octyl dodecyl citrate, hydrolyzed soy protein/dimethicone copolyol acetate, dimethiconol, and mixtures thereof.

Examples of suitable water soluble silicone quaterniums nonexclusively include silicone quaternium 13, silicone quaternium 40, quaternium 80 and mixtures thereof, as well as those silicone quaterniums disclosed in U.S. Pat. No. 5,098,979, which is incorporated by reference herein in its entirety.

More preferred water soluble silicone agents include silicone quaternium 13, cetyl triethylmonium dimethicone copolyol phthalate, stearalkonium deimethicone copolyol phthalate, and mixtures thereof.

The second component in the composition of the present invention is a cationic conditioning agent such as a cationic cellulose derivative; a cationic guar derivative; a homopolymer or copolymer of a cationic monomer selected from:
  a. a monomer having the formula II.

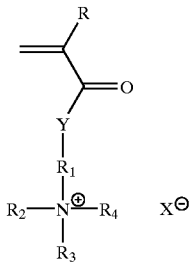
II.

wherein
R is H or $CH_3$,
Y is O or NH,
$R_1$ is an alkylene group having from about 2 to about 6 carbon atoms,
$R_2$, $R_3$ and $R_4$ are each independently an alkyl group or hydroxyalkyl group having from about 1 to about 22 carbon atoms, and
X is a monovalent anion selected from halide and alkyl sulfate having from about 1 to about 4 carbon atoms, or
  b. diallyldimethylammonium chloride, or mixtures thereof.

A suitable cationic cellulose derivative is the polymeric quaternary ammonium salt derived from the reaction of hydroxyethyl cellulose with a trimethylammonium substituted epoxide. The material known as Polyquaternium-10, commercially available from Amerchol Corporation of Edison, N.J. as "Polymer JR-400," is especially useful in this regard.

The cationic guar derivative is preferably a guar hydroxypropyltrimonium chloride, available commercially from Rhone-Poulenc Inc., of Cranbury, N.J. under the tradename, "Jaguar C-17."

Another suitable cationic polymer includes those compounds derived from acrylamidopropyl trimonium chloride which has the formula III:

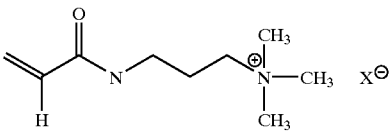
III.

and more preferably is the copolymer of this monomer with acrylamide, the latter of which is available commercially from Allied Colloids, of Suffolk, Va. under the tradename, "Salcare SC60."

Other suitable cationic conditioning polymers are those derived from the monomer diallyldimethylammonium chloride. The homopolymer of this monomer is Polyquaternium-6, which is available commercially from Allied Colloids of Suffolk, Va. under the tradename, "Salcare SC30." The copolymer of diallyldimethylammonium chloride with acrylamide is known as Polyquaternium-7, and is also available from Allied Colloids under the tradename "Salcare SC10." Other suitable polymers include polyquaternium-47, which is available from Calgon Corporation under the tradename, "MERQUAT 2001N."

Most preferred cationic conditioning agents include acrylamidopropyltrimonium chloride/acrylamide copolymer, guar hydroxypropyltrimonium chloride, and mixtures thereof.

The third component in the composition of the present invention is a detergent. By "detergent," it is meant any known surfactant and/or soap that is compatible with the silicone agents and the cationic agents of the cleansing composition, and may nonexclusively include anionic surfactants, nonionic surfactants, cationic surfactants, amphoteric surfactants (including betaine surfactants and zwitterionic surfactants) and mixtures thereof.

Examples of suitable anionic surfactants include, but are not limited to, compounds in classes known as alkyl sulfates, sulfate esters of an alkylphenoxy polyoxyethylene ethanol, alpha-olefin sulfonates, betaalkyloxy alkane sulfonates, alkyl arylsulfonates, alkyl carbonates, alkyl ether carboxylates, fatty acids, sulfosuccinates, alkyl ether sulfosuccinates, sarcosinates, octoxynol phosphates, nonoxynol phosphates, taurates, fatt taurides, sulfated monoglycerides, fatty acid amido polyoxyethylene sulfates, and isethionates and mixtures thereof. Many additional surfactants are described in WO 07/26860 and in McCUTCHEON'S DETERGENTS AND EMULSIFIERS (1989), which are both incorporated herein by reference. These anionic surfactants are generally present in the composition as a neutralized salt in the form of sodium salts, potassium salts, ammonium salts, lithium salts, alkyl ammonium salts, or hydroxyalkyl ammonium salts. Preferred anionic surfactants are alkyl sulfates, alkyl ether sulfates, alkyl phosphates, amino acid salts such as N-acyl-L-glutamate, α-olefin sulfonates, alkyl sarcosinates, alkyl benzene sulfonates, acyl isethionates, alkyl sulfosuccinates, acyl methyl taurides, and mixtures thereof, with sodium C14–16 olefin sulfonate, ammonium lauryl sulfate, sodium trideceth sulfate, sodium laureth sulfate, disodium laureth sulfosuccincite being most preferred.

Examples of suitable nonionic surfactants include, but are not limited to, those set forth in WO 07/26860, with polysorbate 20, long chain alkyl glucosides having alkyl groups containing about 8 carbon atoms to about 22 carbon atoms; coconut fatty acid monoethanolamides such as cocamide MEA; coconut fatty acid diethanolamides, and mixtures thereof, being most preferred. Any amount of cationic surfactants or non-oinic surfactants employed in the detergent base are in addition to the amount of the non-ionic surfactant or cationic surfactant, respectively, that may be included in the vesicle bilayer.

Examples of suitable cationic surfactants include, but are not limited to, those set forth in WO 07/26860, as well as the quaternary ammonium surfactants and quaternary amine surfactants that are not only positiely charged at the pH of the shampoo composition, which generally is about pH 10 or lower, but also are soluble in the shampoo composition. Preferred cationic surfactants nonexclusively include the n-acylamidopropyl dimethylamine oxides such as cocamidopropylamine oxide sold commercially under the tradename "Incromine Oxide C" available from Croda Inc. Parsippany, N.J.

Examples of suitable amphoteric surfactants include, but are not limited to, those set forth in WO 07/26860, i.e., amphocarboxylates, alkyl betaines, amidoalkylbetaines, amidoalkylsultaines, amphophosphates, phosphobetaines, pyrophosphobetaines, carboxyalkyl alkyl polyamines, and mixtures thereof. Preferred amphoteric surfactants include amidoalkylbetaines such as cocamidopropyl betaine available commercially from Goldschmidt Chemical Corporation of Hopewell, Va. under the tradename "Tegobetaine E"; alkyl imidazoline having from about 8 carbon atoms to about 18 carbon atoms in the alkyl group such as Sodium Cocoamphopropionate available commercially from Mona Industries Inc. of Paterson, N.J. under the tradename "Monateric CA-35".

Examples of suitable soaps include fatty acids reacted with potassium, sodium, ammonium, lithium, or a triethanol amine base to form soaps such as, e.g., sodium cocoate or triethanolamine cocoate.

In a preferred embodiment, the detergent is comprised of a mixture of, based upon the total weight of the detergent, from about 0.1 percent to about 30 percent, and preferably from about 1 percent to about 20 percent anionic surfactants, from about 0 percent to about 10 percent, and preferably from about 1 percent to about 7 percent nonionic surfactants, from about 0 percent to about 10 percent, and preferably from about 0 percent to about 4 percent cationic surfactants, and from about 0 percent to about 15 percent, and preferably from about 1 percent to about 10 percent amphoteric surfactants.

In another preferred embodiment, the cleansing composition is comprised of, based upon the total weight of surfactant, from about 50 percent to about 99 percent, and preferably from about 80 percent to about 95 percent, of anionic surfactants preferably selected from the group consisting of alkyl sulfates, alkyl ether sulfates, and mixtures thereof wherein the alkyl group has from about 8 carbon atoms to about 18 carbon atoms, and from about 1 percent to about 20 percent, and preferably from about 5 percent to about 15 percent of amphoteric surfactants, preferably cocamidopropyl betaine.

In another preferred embodiment, the cleansing composition is comprised of, based upon the total weight of surfactant, from about 50 percent to about 99 percent, and preferably from about 70 percent to about 90 percent, of anionic surfactants, preferably those selected from the group consisting of sodium PEG-7 olive oil carboxylate, alkyl sulfates, alkyl ether sulfates, and mixtures thereof wherein the alkyl group has from about 8 carbon atoms to about 18 carbon atoms; from about 1 percent to about 30 percent, and preferably from about 10 percent to about 25 percent of an amphoteric surfactant preferably selected from the group consisting of cocamidopropyl betaine and mixtures thereof; and optionally, from about 0 percent to about 15 percent, and preferably from about 2 percent to about 10 percent of a cationic surfactant such as cocammoniumcarbomoyl chloride.

In embodiments wherein a particulate compound, such as several of the anti-dandruff agents, e.g. zinc pyrithione, that tends to precipitate out of the solution is combined with the cleansing composition, the surfactant is preferable employed in conjunction with a suspending agent, with the latter having the ability of suspending the particulate compound. In those embodiments, the suspending agent-containing cleansing composition may be made by either 1) simultaneously combining the suspending agent with the detergent, the silicone agents, and the cationic conditioners, or preferably, 2) pre-mixing the suspending agent with the detergent component, then combining the resulting mixture with the silicone agents and the cationic conditioners.

Examples of suitable suspending agents nonexclusively include: 1) acrylate polymers and copolymers thereof such as the Acrylates/Aminoacrylates C10–30 Alkyl PEG-20 Itaconate copolymer available commercially from National Starch and Chemical Corporation of Bridgewater, N.J. under the trade name "Structure Plus"; 2) fatty acyl derivatives, wherein the acyl group has the structure IV:

IV.

wherein $R_{10}$ comprises a carbon chain having from about 7 carbon atoms to about 21 carbon atoms that is either saturated or unsaturated and is either substituted or unsubstituted with, for example, hydroxyl groups; 3) esters of long chain fatty acids, wherein the fatty acids have the structure V:

V wherein $R_{11}$ is an alkyl group having from 8 carbon atoms to about 30 carbon atoms, and $R_{12}$ is an alkyl group having from about 8 carbon atoms to about 30 carbon atoms, such as stearyl stearate; 4) alkyl dimethylamine oxides wherein the alkyl group has from about 8 carbon atoms to about 18 carbon atoms as disclosed in U.S. Pat. No. Re. 34,584, which is incorporated by reference herein in its entirety; 5) methylvinylether/maleic anhydride copolymer crosslinked with 1,9-decadiene PolyVM/MA (PVM/MA decadiene crosspolymer) available from International Specialty Products under the tradename, "Stabileze 06 & QM;" 6) cellulose derivatives such as methylcellulose, hydroxybutyl methylcellulose, hydroxypropylcellulose, hydroxypropyl methylcellulose, hydroxyethyl ethylcellulose, hydroxyethyl cellulose, and mixtures thereof; 7) Distearyl Phthalic Amide available from Stepan Company under the tradename "Stepan SAB-2," 8) Di(hydrogenated) Tallow Phthalic Amide available from Stepan Company under the tradename "Stepan TAB-2"; 9) primary amines having a fatty alkyl group with at least about 16 carbon atoms such as palmitate amine and stearamine; 10) polyacrylic acids such as carbomers, which are available from B.F. Goodrich Company under the tradename, "Carbopol"; 11) polysaccharide gums such as xanthan gum; 12) colloidal clays such as benzyl dimethyl hydrogenated tallow ammonium montmorillonite (Bentone 27); 13) colloidal silica; and 14) mixtures thereof. Examples of suitable fatty acyl derivatives include ethylene glycol distearate, ethylene glycol monostearate, and alkanolamides such as cocamide MEA, and mixtures thereof.

Preferred suspending agents include carbomer, hydroxyethyl cellulose, methylvinylether/maleic anhydride copolymer crosslinked with 1,9-decadiene PolyVM/MA (PVM/MA decadiene crosspolymer), and Acrylates/Aminoacrylates C10–30 Alkyl PEG-20 Itaconate Copolymer, with Acrylates/Aminoacrylates C10–30 Alkyl PEG-20 Itaconate Copolymer being most preferred.

The suspending agent is preferably used in an amount effective for suspending the particulate compound. Although such amount may vary dependent upon, for example, the type of particulate compound selected, the viscosity of the formulation desired, and the stability of the formulation, typically the amount of suspending agent may range, based upon the total weight of the detergent, from about 0 percent to about 5 percent, and preferably from about 0.01 percent to about 1 percent.

Other optional ingredients that may be included in the cleansing composition nonexclusively include commercially available pearlescent or opacifying agents, thickeners, chelating agents, colorants, fragrance, preservatives, pH adjustors, conditioning agents, and mixtures thereof.

Suitable pearlescent or opacifying agents which are respectively present in an amount, based upon the total weight of the composition, of from about 0 percent to about 3 percent, preferably from about 0.25 percent to about 2.5 percent, and more preferably, from about 0.5 percent to about 1.5 percent. Examples of suitable pearlescent or opacifying agents include, but are not limited to mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula X:

HO—(JO)$_a$—H  X.

wherein
J is an alkylene group having from about 2 to about 3 carbon atoms; and
a is 2 or 3;
fatty alcohols containing from about 16 to about 22 carbon atoms; fatty esters of the formula XI:

KCOOCH$_2$L  XI.

wherein K and L dependently contain from about 15 to about 21 carbon atoms;
inorganic solids insoluble in the shampoo composition, and mixtures thereof.

In a preferred embodiment, the pearlescent or opacifying agent is introduced to the shampoo composition as a preformed, stabilized aqueous dispersion, such as that commercially available from Henkel Corporation of Hoboken, N.J. under the tradename, "Euperlan PK-3000." This material is a combination of glycol distearate (the diester of ethylene glycol and stearic acid), Laureth-4 (CH$_3$(CH$_2$)$_{10}$CH$_2$(OCH$_2$CH$_2$)$_4$OH) and cocamidopropyl betaine and preferably is in a weight percent ratio of from about 25 to about 30: about 3 to about 15: about 20 to about 25, respectively.

Examples of suitable chelating agents include those which are capable of protecting and preserving the composition of this invention. Preferably, the chelating agent is EDTA, and more preferably is tetrasodium EDTA available commercially from Dow Chemical Company of Midland, Mich. under the tradename, "Versene 100XL" and is present in an amount, based upon the total weight of the composition, from about 0 to about 0.5 percent, and preferably from about 0.05 percent to about 0.25 percent. Other suitable chelating agents include parabens such as methyl paraben, propyl paraben, butyl paraben, isomethyl paraben, isopropyl paraben, isobutyl paraben, sodium benzoate, iodopropynyl butylcarbamate which is commercially available as "Glycacil L" from Lonza, Inc., and mixtures thereof. Suitable preservatives include Quaternium-15, available commercially as "Dowicil 200" from the Dow Chemical Corporation of Midland, Mich., and are present in the composition in an amount, based upon the total weight of the composition, from about 0 to about 0.2 percent and preferably from about 0.05 percent to about 0.10 percent.

The above described cleansing composition may be prepared by combining the desired components in a suitable container and mixing them under ambient conditions in any conventional mixing means well known in the art, such as a mechanically stirred propeller, paddle, and the like. Although the order of mixing is not critical, it is preferable to pre-blend certain components, such as the fragrance and the nonionic surfactant before adding such components into the main mixture.

The composition of this invention can be formulated in a variety of dosage forms for topical application that include, but are not limited to, for example, washes, baths, lotions, creams, ointments, sprays, aerosols, skin patches, soap, mousses, tonics, gels, solids (e.g. sticks) or the like which is designed to be left on the skin and not washed shortly after application. Alternatively, the composition may be applied to the desired area in the form of, for example, a lotion, cream, gel, soap, shampoo or the like which is designed to be rinsed off within a given amount of time after application.

Another preferred embodiment of the present invention is directed to a delivery system for delivering benefit agents to the hair, nails, and scalp comprised of a) at least one water soluble silicone agent; and b) at least one, and more preferably at least two cationic conditioning compounds. Preferably, the delivery system is comprised of, based upon the total weight of the delivery system, a) from about 0.001 percent to about 10 percent, and preferably from about 0.01 percent to about 5 percent of at least one water soluble silicone agent; and b) from about 0.001 percent to about 5 percent, and preferably from about 0.01 percent to about 2 percent of at least one, and preferably at least two cationic conditioning compounds.

In embodiments wherein it is desirable to deposit hydrophilic benefit agents, e.g. salicylic acid, alpha hydroxy acids, vitamins, proteins, and peptides, onto and/or into the skin, hair, and nails, it is preferable to apply thereto the benefit agent in the delivery system composition comprised of at least two cationic conditioning compounds, which preferably are guar hydroxypropyltrimonium chloride and acrylaminopropyltrimonium chloride/acrylamide copolymer; and more preferably with the combination of at least 2 cationic conditioning compounds, which are preferably guar hydroxypropyltrimonium chloride and acrylaminopropyltrimonium chloride/acrylamide copolymer, and at least one water soluble silicone compound, which preferably is a silicone quaternium-13. It is most preferable to apply the hydrophilic benefit agent in a delivery system comprised of at least 2 cationic conditioning compounds, which preferably are guar hydroxypropyltrimonium chloride and acrylamidopropyltrimonium chloride/acrylamide copolymer, and at least two water soluble silicone compounds, one of which is preferably a silicone quaternium-13.

In embodiments wherein it is desirable to deposit hydrophobic benefit agents, i.e. elubiol, ketoconazole, retinol and derivatives thereof, onto and/or into the skin, nails, and/or hair, it is preferable to apply thereto the hydrophobic benefit agent in a delivery system composition comprised of at least 2 cationic conditioning compound, which preferably are guar hydroxypropyltrimonium chloride and acrylamiiopropyltrimonium chloride/acrylamide copolymer and at least one water soluble silicone compound, which preferably is a silicone quaternium-13. It is more preferable to apply the hydrophobic benefit agent in a delivery system comprised of at least 2 cationic conditioning compounds, which preferably are guar hydroxypropyltrimonium chloride and acrylamidopropyltrimonium chloride/acrylamide copolymer, and at least two water soluble silicone compounds, one of which is preferably a silicone quaternium-13.

In embodiments wherein it is desirable to deposit a thin coating of conditioner on the hair fiber, it is desirable to apply thereto a composition comprised of at least two cationic agents and at least one water soluble silicone, the latter of which preferably is cetyl triethylmonium dimethicone copolyol phthalate. Suitable depositing conditioners nonexclusively include the silicone agents and cationic conditioning agents described herein as well as other known conditioners.

In addition to combining a benefit agent along with the delivery system, another embodiment of the present invention is directed to combining an optional benefit agent along with the above-described cleansing composition. By "benefit agent," it is mean any active ingredient that is to be delivered into and/or onto the skin at a desired location, such as a cosmetic agent or a pharmaceutical agent. By "cosmetic agent," it is meant any ingredient that is appropriate for cosmetically treating, providing nutrients to, and/or conditioning the hair and/or skin via topical application. By "pharmaceutical agent," it is mean any drug that is either hydrophobic or hydrophilic in nature and appropriate for topical use. As used herein "medicament agents" include those agents capable of promoting recovery from injury and illness.

Examples of suitable benefit agents include, but are not limited to, depigmentation agents; reflectants; thickening agents; detangling/wet combing agents; film forming polymers; humectants; amino acid agents; antimicrobial agents; allergy inhibitors; anti-acne agents; anti-aging agents; anti-wrinkling agents, antiseptics; analgesics; antitussives; anti-pruritics; local anesthetics; anti-hair loss agents; hair growth promoting agents; hair growth inhibitor agents, antihistamines; antiinfectives; inflammation inhibitors; anti-emetics; anticholinergics; vasoconstrictors; vasodilators; wound healing promoters; peptides, polypeptides and proteins; deodorants and anti-perspirants; medicament agents; skin emollients and skin moisturizers; hair conditioners; hair softeners; hair moisturizers; vitamins; tanning agents; skin lightening agents; antifungals such as antifungals for foot preparations; depilating agents; shaving preparations; external analgesics; perfumes; counterirritants; hemorrhoidals; insecticides; poison ivy products; poison oak products; burn products; anti- diaper rash agents; prickly heat agents; make-up preparations; vitamins; amino acids and their derivatives; herbal extracts; retinoids; flavoids; sensates; anti-oxidants; skin conditioners; hair lighteners; chelating agents; cell turnover enhancers; coloring agents; pigments; sunscreens and the like, and mixtures thereof. The amount of certain cleansing composition/delivery system compounds for the benefit agent purposes set forth below is in addition to the amount of the same compound that may be desired for use in the cleansing composition/delivery system therefor.

Examples of suitable reflectants nonexclusively include mica, alumina, calcium silicate, glycol dioleate, glycol distearate, silica, sodium magnesium fluorosilicate, and mixtures thereof.

Examples of suitable UV absorbers include benzophenone, bornelone, butyl paba, cinnamidopropyl trimethyl ammonium chloride, disodium distyrylbiphenyl disulfonate, paba, potassium methoxycinnamate, and mixtures thereof.

Commercially available thickening agents that are capable of imparting the appropriate viscosity to the conditioning shampoo compositions are suitable for use in this invention. If used, the thickener should be present in the shampoo compositions in an amount sufficient to raise the Brookfield viscosity of the composition to a value of between about 500 to about 10,000 centipoise. Examples of suitable thickening agents nonexclusively include: mono or diesters of polyethylene glycol of formula VI.

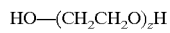
$$HO—(CH_2CH_2O)_zH \qquad \text{VI.}$$

wherein z is an integer from about 3 to about 200; fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. More specifically, suitable thickening agents nonexclusively include behenalkonium chloride; cetyl alcohol, quaternium 46, PG-hydroxyethyl cellulose, cocodimonium chloride, polyquaternium 6, polyquaternium 7, quaternium 18, PEG-18 glycerol oleate/cocoate, a mixture of acrylates/spirit 50 acrylate copolymer, laureth 3 and propylene glycol, which is commercially available from Goldschmidt under the tradename "Antil 208," a mixture of cocamidopropylbetaine and glyceryl laurate which is commercially available from Goldschmidt under the tradename, "Antil HS60," a mixture of propylene glycol, PEG 55, and propylene glycol oleate, which is commercially available from Goldschmidt under the tradename, "Antil 414 liquid," and mixtures thereof. Preferred thickeners include polyethylene glycol ester, and more preferably PEG-150 distearate which is available from the Stepan Company of Northfield, Ill. or from Corniel, S.p.A of Bologna, Italy under the tradename, "PEG 6000 DS".

Suitable detangling/wet combing agents nonexclusively include dioleoylamidoethyl hydroxythylmonium methosulfate, di(soyoylethyl) hydroxyethylmonium methosulfate, hydroxyethyl behenamidopropyl dimonium chloride, olealkonium chloride, polyquaternium 47, stearalkonium chloride, tricetylmonium chloride, and mixtures thereof.

Suitable film forming polymers include those that, upon drying, produce a substantially continuous coating or film on the hair, skin, or nails. Nonexclusive examples of suitable film forming polymers include acrylamidopropyl trimonium chloride/acrylamide copolymer; corn starch/ acrylamide/ sodium acrylate copolymer; polyquaternium 10; polyquaternium 47; polyvinylmethyl/maleic anhydride copolymer; styrene/acrylates copolymers; and mixtures thereof.

Comnmercially available humectants which are capable of providing moisturization and conditioning properties to the cleansing composition are suitable for use in the present invention. The humectant is preferably present in an amount of from about 0 percent to about 10 percent, more preferably from about 0.5 percent to about 5 percent, and most preferably from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, pentylene glycol, dipropylene glycol, and mixtures thereof; 2) polyalkylene glycol of the formula VII:

$$HO—(R''O)_b—H \qquad \text{VII.}$$

wherein R" is an alkylene group having from about 2 to about 4 carbon atoms and b is an integer of from about 1 to about 10, such as PEG 4; 3) polyethylene glycol ether of methyl glucose of formula VIII:

$$CH_3—C_6H_{10}O_5—(OCH_2CH_2)_c—OH \qquad \text{VIII.}$$

wherein c is an integer from about 5 to about 25;
4) urea; 5) fructose; 6) glucose; 7) honey; 8) lactic acid; 9) maltose; 10) sodium glucuronate; and 11) mixtures thereof, with glycerine being the preferred humectant.

Suitable amino acid agents include amino acids derived from the hydrolysis of various proteins as well as the salts, esters, and acyl derivatives thereof. Examples of such amino acid agents nonexclusively include amphoteric amino acids such as alkylamido alkylamines, i.e. stearyl acetyl glutamate, capryloyl silk amino acid, caprylol collagen amino acids; capryloyl kertain amino acids; capryloyl pea amino acids; cocodimonium hydroxypropyl silk amino acids; corn gluten amino acids; cysteine; glutamic acid; glycine; hair keratin amino acids; hair amino acids such as aspartic acid, threonine, serine, glutamic acid, proline, glycine, alanine, half-cystine, valine, methionine, isoleucine, leucine, tyrosine, phenylalanine, cysteic acid, lysine, histidine, arginine, cysteine, tryptophan, citrulline; lysine; silk amino acids, wheat amino acids; and mixtures thereof.

Suitable proteins include those polymers that have a long chain, i.e. at least about 10 carbon atoms, and a high molecular weight, i.e. at least about 1000, and are formed by self-condensation of amino acids. Nonexclusive examples of such proteins include collagen, deoxyribonuclease, iodized corn protein; keratin; milk protein; protease; serum protein; silk; sweet almond protein; wheat germ protein; wheat protein; wheat protein, alpha and beta helix of keratin proteins; hair proteins, such as intermediate filament proteins, high-sulfur proteins, ultrahigh-sulfur proteins, intermediate filament-associated proteins, high-tyrosine proteins, high-glycine tyrosine proteins, tricohyalin, and mixtures thereof.

Examples of suitable vitamins nonexclusively include vitamin B complex; including thiamine, nicotinic acid, biotin, pantothenic acid, choline, riboflavin, vitamin B6, vitamin B12, pyridoxine, inositol, camitine; vitamins A,C, D,E,K and their derivatives such as vitamin A palmitate and pro-vitamins, e.g. (i.e. panthenol (pro vitamin B5) and panthenol triacetate) and mixtures thereof.

Examples of suitable antibacterial agents nonexclusively include bacitracin, erythromycin, neomycin, tetracycline, chlortetracycline, benzethonium chloride, phenol, and mixtures thereof.

Examples of suitable skin emollients and skin moisturizers nonexclusively include mineral oil, lanolin, vegetable oils, isostearyl isostearate, glyceryl laurate, methyl gluceth 10, methyl gluceth 20 chitosan, and mixtures thereof.

Examples of suitable hair conditioners nonexclusively include quaternized compounds such as behenamidopropyl PG-dimonium chloride, tricetylammonium chloride, dihydrogenated tallowamidoethyl hydroxyethylmonium methosulfate, and mixtures thereof as well as lipophilic compounds like cetyl alcohol, stearyl alcohol, hydrogenated polydecene, and mixtures thereof.

An example of a suitable hair softener nonexclusively includes silicone compounds, such as those that are either non-volatile or volatile and those that are water soluble or water insoluble. Examples of suitable silicones include organo-substituted polysiloxanes, which are either linear or cyclic polymers of monomeric silicone/oxygen monomers and which nonexclusively include cetyl dimethicone; cetyl triethylammonium dimethicone copolyol phthalate; cyclomethicone; dimethicone copolyol; dimethicone copolyol lactate; hydrolyzed soy protein/dimethicone copolyol acetate; silicone quaternium 13; stearalkonium dimethicone copolyol phthalate; stearamidopropyl dimethicone; and mixtures thereof.

Examples of suitable hair moisturizers nonexclusively include panthenyl ethyl ether, phytantriol, and mixtures thereof.

Examples of sunscreen agents nonexclusively include butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, padimate o, red petrolatum, and mixtures thereof.

An example of a suitable tanning agent nonexclusively includes dihydroxyacetone.

Examples of skin lightening agents nonexclusively include hydroquinone, catechol and its derivatives, ascorbic acid and its derivatives, and mixtures thereof.

Examples of suitable insecticides (including insect repellents, anti-scabies and anti-lice treatments) nonexclusively include permethrin, pyrethrin, piperonyl butoxide, imidacloprid, N,N-diethyl toluamide, which refers to the material containing predominantly the meta isomer, i.e., N,N-diethyl-m-toluamide, which is also known as DEET; compounds of the formula IX

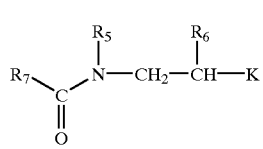

wherein
R$_5$ is a branched or unbranched alkyl group having about 1 to about 6 carbon atoms;
R$_6$ is H, methyl or ethyl;
R$_7$ is a branched or unbranched alkyl or alkoxy group having from about 1 to about 8 carbon atoms; and K is a —CN or a —COOR$_8$ group, wherein
R$_8$ is a branched or unbranched alkyl group having from about 1 to about 6 carbon atoms,
natural or synthetic pyrethroids, whereby the natural pyrethroids are contained in pyrethrum, the extract of the ground flowers of *Chrysanthemum cinerariaefolium* or *C. coccineum*; and mixtures thereof. Within the structure of Formula IX. are ethyl 3-(N-butylacetamido)propionate, wherein R$_7$ is a CH$_3$ group, R$_5$ is an n-butyl group, R$_6$ is H, K is COOR$_8$ and R$_8$ is ethyl, which is available commercially from Merck KGaA of Darmstadt, Germany under the name, "Insect Repellent 3535."

An example of an anti fungal for foot preparations nonexclusively includes tolnaftate.

Examples of suitable depilating agents nonexclusively include calcium thioglycolate, magnesium thioglycolate, potassium thioglycolate, strontium thioglycolate, and mixtures thereof.

Examples of suitable external analgesics and local anesthetics nonexclusively include benzocaine, dibucaine, benzyl alcohol, camphor, capsaicin, capsicum, capsicum oleoresin, juniper tar, menthol, methyl nicotinate, methyl salicylate, phenol, resorcinol, turpentine oil, and mixtures thereof.

Examples of suitable antiperspirants and deodorants nonexclusively include aluminium chlorohydrates, aluminium zirconium chlorohydrates, and mixtures thereof.

Examples of suitable counterirritants nonexclusively include camphor, menthol, methyl salicylate, peppermint and clove oils, ichtammol, and mixtures thereof.

An example of a suitable inflammation inhibitor nonexclusively includes hydrocortisone.

Examples of suitable hemorrhoidal products nonexclusively include the anesthetics such as benzocaine, pramoxine hydrochloride, and mixtures thereof; antiseptics such as benzethonium chloride; astringents such as zinc oxide, bismuth subgallate, balsam Peru, and mixtures thereof; skin protectants such as cod liver oil, vegetable oil, and mixtures thereof.

Examples of suitable make-up preparations nonexclusively include components for lipstick, rouge, blush, eye liner, eyeshadow powder, mascara, face powder, and mixtures thereof.

One preferred type of benefit agent includes those therapeutic components that are effective in the treatment of dandruff, seborrheic dermatitis, and psoriasis as well as the symptoms associated therewith. Examples of such suitable benefits agents nonexclusively include zinc pyrithione, shale oil and derivatives thereof such as sulfonated shale oil, selenium sulfide, sulfur; salicylic acid; coal tar; povidone-iodine, imidazoles such as ketoconazole, dichlorophenyl imidazolodioxalan, which is commercially available from Janssen Pharmaceutica, N.V., under the tradename, "Elubiol", clotrimazole, itraconazole, miconazole, climbazole, tioconazole, sulconazole, butoconazole, fluconazole, miconazolenitrite and any possible stereo isomers and derivatives thereof such as anthralin; piroctone olamine (Octopirox); selenium sulfide; ciclopirox alamine; anti-psoriasis agents such as vitamin D analogs, e.g. calcipotriol, calcitriol, and tacaleitrol; vitamin A analogs such as esters of vitamin A, e.g. vitamin A palmitate, retinoids, retinols, and retinoic acid; corticosteroids such as hydrocortisone, clobetasone, butyrate, clobetasol propionate and mixtures thereof.

Most preferred benefit agents nonexclusively include sulfonated shale oil, elubiol, 6-(1-piperidinyl)-2,4-pyrimidinediamine-3-oxide, finasteride, ketoconazole, salicylic acid, zinc pyrithione, coal tar, benzoyl peroxide, selenium sulfide, hydrocortisone, sulfur, menthol, pramoxine hydrochloride, tricetylammonium chloride, polyquaternium 10, panthenol, panthenol triacetate, vitamin A and derivatives thereof, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, retinol, erthromycin, tretinoin, and mixtures thereof.

The amount of benefit agent to be combined with the cleansing composition or the delivery system may vary depending upon, for example, the resulting benefit desired and the sensitivity of the user to the benefit agent. Unless otherwise expressed herein, preferably the benefit agent is present in the cleansing composition or delivery system in an amount, based upon the total weight of the composition or delivery system, from about 0.001 percent to about 20 percent, and preferably from about 0.001 percent to about 10 percent, and more preferably from about 0.001 percent to about 5 percent.

Another embodiment of the present invention is directed to a method for enhancing the deposition of benefit agents which comprises topically administering to a desired location on a human or animal the delivery system composition as described above combined with an effective amount of a benefit agent and an optional detergent. While the frequency and amount of the delivery system to be applied will depend upon, for example, the type and amount of benefit agent available, the intended usage of the final composition, i.e. therapeutic versus maintenance regimen, the amount and type of detergent present, and the sensitivity of the individual user to the delivery system, typically the delivery system of the present invention should be topically applied to affected body parts at regular intervals, and preferably from about 2 to about 14 times per week. More preferably, the delivery system composition is applied more frequently during the initial stages of treatment, e.g. from about 5 to about 7 times per week until the desired effect is achieved, then less frequently when maintenance is desired, e.g. from about 2 to about 5 times per week.

In a preferred embodiment wherein the delivery system composition containing a benefit agent is incorporated into a shampoo, the shampoo is applied to wet hair, then the hair is washed in accordance with known practices. More preferably, the composition remains on the hair for greater than about 0 to about 10 minutes, and preferably from about 1 to about 5 minutes before rinsing.

An alternative preferred embodiment of the present invention is directed to a method for treating hair loss, such as hair loss resulting from alopecia, comprising topically applying the above-described delivery system composition, the hair loss benefit agent, and the optional detergent, to a desired location on an animal or human, wherein the benefit agent is comprised of an effective amount of a hair loss treatment agent such as minoxidil or mixture thereof. As used herein, "hair loss treatment agents" shall include agents capable of growing hair and/or agents capable of preventing the loss of hair. By "effective amount," it is meant an amount effective for treating hair loss and preferably may range from, based upon the total weight of the cleansing composition/delivery system, from about 0.001 percent to about 20 percent, and preferably from about 1 percent to about 5 percent.

Examples of benefit agents suitable for treating hair loss include, but are not limited to potassium channel openers or peripheral vasodilators such as minoxidil, diazoxide, and compounds such as N*-cyano-N-(tert-pentyl)N'-3-pyridinyl-guanidine ("P-1075") as disclosed in U.S. Pat. No. 5,244,664, which is incorporated herein by reference; vitamins, such as vitamin E and vitamin C, and derivatives thereof such as vitamin E acetate and vitamin C palmitate; hormones, such as erythropoietin, prostaglandins, such as prostaglandin El and prostaglandin F2-alpha; fatty acids, such as oleic acid; diruretics such as spironolactone; heat shock proteins ("HSP"), such as HSP 27 and HSP 72; calcium channel blockers, such as verapamil HCL, nifedipine, and diltiazemamiloride; immunosuppressant drugs, such as cyclosporin and Fk-506; 5 alpha-reductase inhibitors such as finasteride; growth factors such as, EGF, IGF and FGF; transforming growth factor beta; tumor necrosis factor; non-steroidal ant-inflammatory agents such as benoxaprofen; retinoids such as tretinoin; cytokines, such as IL-6, IL-1 alpha, and IL-1 beta; cell adhension molecules such as ICAM; glucorcorticoids such as betametasone; botanical exracts such as aloe, clove, ginseng, rehmannia, swertia, sweet orange, zanthoxylum, Serenoa repens (saw palmetto), Hypoxis rooperi, stinging nettle, pumpkin seeds, and rye pollen; other botanical exracts including sandlewool, red beet root, chrysanthemum, rosemary, burdock root and other hair growth promoter activators which are disclosed in DE 4330597 which is incorporated by reference in its entirety herein; homeopathic agents such as Kalium Phosphoricum D2, Azadirachta indica D2, and Joborandi DI; genes for cytokines, growth factors, and male-pattered baldness; antifungals such as ketoconazole and elubiol; antibiotics such as streptomycin; proteins inhibitors such as cyclohexdmide; acetazolamide; benoxaprofen; corisone; ditiazem; hexachlorobenzene; hydantoin; nifedipine; penicillamine; phenothaiazines; pinacidil; psoralens, verapamil; zidovudine; alpha-glucosylated rutin having at least one of the following rutnis: quercetin, isoquercitrin, hespeddin, naringin, and methylhesperidin, and flavonoids and transglycosidated derivatives thereof which are all disclosed in JP 7002677, which is incorporated by reference in its entirety herein; and mixtures thereof.

Preferred hair loss treatment agents include 6(I-piperdinyl)-2,4-pyrimidinediamine-3-oxide, N'-cyano-N-(tert-pentyl)-N'-3-pyridinyl-guanidine, finasteride, retinoids and derivatives thereof, ketoconazole, elubiol or mixtures thereof.

Another embodiment of the present invention is directed to a method for inhibiting hair growth comprising topically applying the above-described delivery system composition combined with a benefit agent and an optional detergent, to a desired area on an animal or human for inhibiting hair growth, wherein the benefit agent is comprised of an effective amount of a hair growth inhibiting agent. In a preferred embodiment, the delivery system composition contains, based upon the total weight of the composition, from about 0.001 percent to about 20 percent, and preferably from about 0.01 percent to about 5 percent hair growth inhibiting agent.

Examples of benefit agents suitable for use in inhibiting hair growth include: serine proteases such as trypsin; vitamins such as alpha-tocophenol (vitamin E) and derivatives thereof such as tocophenol acetate and tocophenol palmitate; antineoplastic agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon alpha, interferon alpha-2a and interferon alpha-2b; retinoids, such as retinol (vitamin A), isotretinoin: glucocorticoids such as betamethasone, and dexamethosone; antihyperlipidaemic drugs, such as triparanol and clofibrate; thallium; mercury; albendazole; allopurinol; amiodarone; amphetamines; androgens; bromocriptine; butyrophenones; carbamazepine; cholestyramine; cimetidine; clofibrate; danazol; desipramine; dixyrazine; ethambutol; etionamide; fluoxetine; gentamicin; gold salts; hydantoins; ibuprofen; imipramine; immunoglobulins; indandiones; indomethacin; intraconazole; levadopa; maprotiline; methysergide; metoprolol; metyrapone; nadolol; nicotinic acid; potassium thiocyanate; propranolol; pyridostimine; salicylates; sulfasalazine; terfenadine; thiamphenicol; thiouracils; trimethadione; troparanol; valproic acid; and mixtures thereof.

Preferred hair growth inhibitory agents include serene proteases, retinol, isotretinoin, betamethoisone, alpha-tocophenol and derivatives thereof, or mixtures thereof.

Another preferred embodiment of the present invention is directed to a method for treating acne and for reducing the signs of aging, i.e. wrinkles, fine lines, and other manifestations of photodamage, comprising topically applying the above-described delivery system composition, the relevant benefit agent, and the optional detergent to the skin of an animal or human at a desired area, wherein the benefit agent is comprised of an effective amount of an anti-acne agent or an antiaging agent, respectively.

Examples of suitable anti-aging agents include, but are not limited to inorganic sunscreens such as titanium dioxide and zinc oxide; organic sunscreens such as octyl-methyl cinnamates and derivatives thereof; retinoids; vitamins such as vitamin E, vitamin A, vitamin C, vitamin B, and derivatives thereof such as vitamin E acetate, vitamin C palmitate, and the like; antioxidants including beta carotene, alpha hydroxy acid such as; glycolic acid, citric acid, lactic acid, malic acid, mandelic acid, ascorbic acid, alpha-hydroxbutyric acid, alpha-hydroxyisobutyric acid, alpha-hydroxyisocaproic acid, atrrolactic acid, alpha-hydroxyisovaleric acid, ethyl pyruvate, galacturonic acid, glucopehtonic acid, glucopheptono 1,4-lactone, gluonic acid, gluconolactone, glucuronic acid, glucurronolactone, glycolic acid, isopropyl pyruvate, methyl pyruvate, mucic acid, pyruvia acid, saccharic acid, saccaric acid 1,4-lactone, tartaric acid, and tatronic acid; beta hydroxy acids such as beta-hydroxybutyic acid, beta-phenyl-lactic acid, beta-phenylpyruvic acid; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, safflower, and mixtures thereof.

Preferred anti-aging agents include retinoids, antioxidants, alpha-hydroxy acids and beta-hydrox acid with retinol and tretinoin being most preferred.

Suitable amounts of anti-aging agents include, based upon the total weight of the delivery system composition and optional detergent, from about 0.01 percent to about 10 percent, and preferably from about 0.04 percent to about 5 percent.

Examples of suitable anti-acne agents include, but are not limited to topical retinoids (tretinoin, isotretinoin, motretinide, adapalene, tazarotene, azelaic acid, retinol); salicylic acid; benzoyl peroxide; resorcinol; antibiotics such as tetracycline and isomers thereof, erythromycin, and the anti-inflammatory agents such as ibuprofen, naproxen, hetprofen: botanical extracts such as alnus, amica, artemisia capillaris, asiasarum root, birth, calendula, chamomile, cnidium, comfrey, fennel, galla rhois, hawthrom, houttuynia, hypericum, jujube, kiwi, licorice, magnolia, olive, peppermint, philodendron, salvia, sasa albomarginata; imidazoles such as ketoconazole and elubiol, and those described in Gollnick, H et al. 196(I) Dermatology Sebaceous Glands, Acne and Related Disorders, 119–157 (1998), which is incorporated by reference herein, and mixtures thereof.

Preferred anti-acne agents include benzoyl peroxide, retinol, elubiol, antibiotics, and salicylic acid, with retinol and tretinoin being most preferred.

Suitable amount of anti-acne agents include, based upon the total weight of the delivery system composition and optional detergent, from about 0.01 percent to about 10 percent, and preferably from about 0.04 percent to about 5 percent.

Another preferred embodiment of the present invention is directed to a method for depigmenting the skin comprising topically applying to skin at a desired area the above-described delivery system composition, the optional detergent, and an effective amount of the depigmentation benefit agent. Suitable effective amounts of depigmentation agents include, based upon the total weight of the delivery system, from about 0.01 percent to about 10 percent, and preferably from about 0.04 percent to about 5 percent.

Examples of suitable depigmentation agents include, but are not limited to retinoids such as retinol; Kojic acid and its derivatives such as, for example, kojic dipalmitate; hydroquinone and it derivtives such as arbutin; transexamic acid; vitamins such as niacin, vitamin C and its deivatives; azelaic acid; placertia; licorice; extracts such as chamomile and green tea, and mixtures thereof, with retinol, Kojic acid, and hydroquinone, being preferred.

An alternative preferred embodiment of the present invention is directed to a method for treatng the symptoms and/or the diseases of dandruff, seborrheic dermatitis and/or psoriasis, comprising topically applying the above-described delivery system composition, the benefit agent and the optional detergent, to a location desired wherein the benefit agent is comprised of an effective amount of a dandruff treatment agent, a seborrheic dermatitis treatment agent, or a psoriasis treatment agent, respectiely. As used herein, "dandruff treatment agent," "seborrheic dermatitis treatment agent," or a "psoriasis treatment agent," respectively, shall include agents capable of treating the symptoms and/or the diseases of dandruff, seborrheic dermatitis, and psoriasis, respectively. By "effective amount," it is meant an amount effective for treating the disease and/or the symptoms associated therewith and preferably may range from, based upon the total weight of the vesicle delivery system and optional detergent, from about 0.001 percent to about 10 percent, and preferably from about 0.01 percent to about 5 percent.

Examples of benefit agents suitable for treating the symptoms and/or the diseases of dandruff, seborrheic dermatitis and/or psoriasis, respectively, nonexclusively include those set forth above with shale oil and derivatives thereof, elubiol, ketoconazole, coal tar, salicylic acid, zinc pyrithione, selenium sulfide, hydrocortisone, sulfur, menthol, pramoxine hydrochloride, and mixtures thereof being particularly preferred.

We have unexpectedly found that the above-described cleansing composition/delivery system is capable of efficiently mediating the deposition and permeation of various benefit agents, such as antidandruff agents, onto and into the skin following topical administration thereto.

We have surprisingly found that the cleansing composition of the present invention is sufficiently stable to resist phase separation even though both an anionic surfactant and cationic components may be present in the composition. Furthermore, the cleansing composition not only effectively cleanses the hair due to the ability to include an anionic surfactant therein, but it also effectively deposits conditioning agents on the hair without exhibiting an excessive build-up thereon, even after repeated shampooing. Consequently, the hair is left in a more manageable, softer, shiny and overall more esthetically pleasing state after only a single application of the composition to the hair.

We have further unexpectedly found that the above-described delivery system is capable of efficiently mediating the deposition and permeation of various benefit agents, such as antidandruff agents, onto and into the skin, hair, and nails, following topical administration thereto.

The invention illustratively disclosed herein suitably may be practiced in the absence of any component, ingredient, or step which is not specically disclosed herein. Several examples are set forth below to further illustrate the nature of the invention and the manner of carrying it out. However, the invention should not be considered as being limited to the details thereof.

EXAMPLES

Example 1

Preparation of Cleansing Shampoo Containing Two Cationic Agents

Shampoos comprised of the following components as set forth in Table 1 were prepared:

TABLE 1

Cleansing shampoo with two cationic depositing enhancing agents.

| | Trade Name | CTFA | % wt/wt | Supplier |
|---|---|---|---|---|
| 1 | DI water | DI water | 72.965 | |
| 2 | Salcare SC 60 | Acrylamidopropyiltrimoniumchloride Acrylamide Copolymer | 0.08 | Ciba Specialties |
| 3 | Jaguar C 17 | Guar Hydroxypropyl Trimonium Chloride | 0.15 | Rhone-Poulenc |
| 4 | Citric Acid Anh | Citric Acid | 0.025 | Roche |
| 5 | Elubiol | Dichlorophenyl Imidazoidioxolan | 0.50 | Janssen Pharm. |
| 6 | Salicylic Acid | Salicylic Acid | 1.00 | Rhone-Poulenc |
| 7 | Cutina AGS | Glycol Distearate | 1.75 | Henkel |
| 8 | Methyl Paraben | Methyl Paraben | 0.20 | Nipa Hardwicke Inc. |
| 9 | Empicol EAC 70 | Ammonium Laureth Sulfate | 3.6 | Albright & Wilson |
| 10 | Empicol AL 70 | Ammonium Lauryl Sulfate | 11.8 | Albright & Wilson |
| 11 | Tego Betaine E | Cocamidopropyl Betaine | 2.43 | Goldschmidt |
| 12 | Tego Betaine F 50 | Cocamidopropyl Betaine | 3.00 | Goldschmidt |
| 13 | Polyox WSR-205 | PEG 14M | 0.05 | Amerchol |

TABLE 1-continued

Cleansing shampoo with two cationic depositing enhancing agents.

| | Trade Name | CTFA | % wt/wt | Supplier |
|---|---|---|---|---|
| 14 | Ninol LMP | Lauramide MEA | 1.00 | Stephan |
| 15 | DL-Panthenol-50% | Panthenol | 0.15 | Roche |
| 16 | Phytantriol | Phytantriol | 0.025 | Roche |
| 17 | Hydrotriticum WAA | Wheat Amino Acid | 0.22 | Croda |
| 18 | Sodium Benzoate | Sodium Benzoate | 0.20 | EM Industries |
| 19 | Versene 100XL | Tetrasodium EDTA | 0.20 | Dow Chemical |
| 20 | BHT | Butylated Hydroxytoluene | 0.10 | EM Industries |
| 21 | Lorena | Fragrance | 0.50 | Creation Aromatiques |
| 22 | Glycacil L | Iodopropynyl butylcarbamate | 0.05 | Lonza |
| 23 | NaOH (25%) | Sodium Hydroxide | QS | Mallinckrodt |
| | Total | | 100.00 | |

Shampoo Process

A vessel was charged with ¾ amount of deionized water (component 1). Components 2, 3 and 4 were added sequentially thereto, both with ten minute intervals between the additions and with mixing at 500 rpm under constant conditions. The resulting mixture was then heated to about 63 to 67° C. with mixing at 500 rpm. Component 5 was then to the mixture. After all the elubiol had dissolved, salicylic acid (component 6) was added thereto with mixing for 15–20 minutes at constant conditions. The resultant mixture was then heated to 70–75° C. and components 7, 8, 9 and 10 were sequentially added under mixing. Component 9 through 13 were sequentially added thereto with mixing under constant conditions. The resultant primary mixture was then cooled to 50° C.

Components 15, 16, 20 and 21 were combined in a separate beaker at 25–30° C. to form a premixture. After cooling the primary mixture to 50° C., component 14, component 17, the premixture, component 18, component 19 and component 22 were sequentially added thereto with mixing. Sodium hydroxide was added thereto with mixing to adjust the pH to about 5.3–5.7. The mixture was then continuously mixed and cooled to about 25–30° C. The remaining amount of deionized water was added to the final volume and was mixed at 500 rpm until uniform.

Example 2

Preparation of Cleansing Shampoo Containing Three Cationic Agents

Shampoos comprised of the following components as set forth in Table 2 were prepared:

TABLE 2

Cleansing shampoo with three cationic deposition enhancing agents.

| | Trade Name | CTFA | % wt/wt | Supplier |
|---|---|---|---|---|
| 1 | DI water | DI water | 72.665 | |
| 2 | Salcare SC 60 | Acrylamidopropylitrimoniumchloride Acrylamide Copolymer | 0.08 | Ciba Specialty |
| 3 | Jaguar C 17 | Guar Hydroxypropyl Trimonium Chloride | 0.15 | Rhone-Poulenc |
| 4 | Citric Acid Anh | Citric Acid | 0.025 | Roche |
| 5 | Cutina AGS | Glycol Distearate | 1.75 | Henkel Corporation |
| 6 | Methyl Paraben | Methyl Paraben | 0.20 | Nipa Hardwicke Inc. |
| 7 | Merquat 2001 | Polyquaternium 47 | 0.30 | Calgon |
| 8 | Empicol EAC 70 | Ammonium Laureth Sulfate | 3.6 | Albright & Wilson |
| 9 | Empicol AL 70 | Ammonium Lauryl Sulfate | 11.8 | Albright & Wilson |
| 10 | Tego Betaine E | Cocamidopropyl Betaine | 2.43 | Goldschmidt |
| 11 | Tego Betaine F 50 | Cocamidopropyl Betaine | 3.00 | Goldschmidt |
| 12 | Elubiol | Dichlorophenyl Imidazoldioxolan | 0.50 | Janssen Pharm. |
| 13 | Salicylic Acid | Salicylic Acid | 1.00 | Rhone-Poulenc |
| 14 | Polyox WSR-205 | PEG 14M | 0.05 | Amerchol |
| 15 | Ninol LMP | Lauramide MEA | 1.00 | Stepan |
| 16 | DL-Panthenol-50% | Panthenol | 0.15 | Roche |
| 17 | Phytantriol | Phytantriol | 0.025 | Roche |
| 18 | Hydrotriticum WAA | Wheat Amino Acid | 0.22 | Croda |
| 19 | Sodium Benzoate | Sodium Benzoate | 0.20 | EM Industries |
| 20 | Versene 100XL | Tetrasodium EDTA | 0.20 | Dow Chemical |
| 21 | BHT | Butylated Hydroxytoluene | 0.10 | EM Industries |
| 22 | Lorena | Fragrance | 0.50 | Creation Aromatiques |
| 23 | Glycacil L | Iodopropynyl butylcarbamate | 0.05 | Lonza |
| 24 | NaOH (25%) | Sodium Hydroxide | QS | Mallinckrodt |
| | Total | | 100.00 | |

Shampoo Process

A vessel was charged with ¾ amount of deionized water (component 1). Components 2, 3 and 4 were added sequentially, with ten minute intervals between the additions and with mixing at 500 rpm under constant conditions. The resulting mixture was then heated to about 70 to 75° C. with mixing at 500 rpm. Component 5 and 6 were added and mixed at 500 rpm until dispersed for about 15 to 25 minutes. At 70 to 75° C., components 9 through 11 were added with mixing.

After cooling the resultant mixture to about 63 to 67° C., elubiol, salicylic acid (component 6) and component 14 were added sequentially thereto with mixing until the latter three components were completely dispersed. The resultant primary mixture was then cooled to 50° C.

Components 15, 16, 20 and 21 were combined in a separate beaker at 25–30° C. to form a premixture). After cooling the primary mixture to 50° C., components 15 and 18 were added thereto. The premixture followed by components 19, 20 and 23 were then added thereto sequentially with mixing. Sodium hydroxide was then added thereto with mixing to adjust the the pH to about 5.3–5.7. The mixture was continuously mixed and cooled to about 25–30° C. The remaining amount of deionized water was added to the final volume and was mixed at 500 rpm until uniform.

Shampoo Process

A vessel was charged with ¾ amount of deionized water (component 1). Components 2, 3 and 4 were added sequentially, with ten minute intervals between the additions and with mixing at 500 rpm under constant conditions. The resulting mixture was then heated to about 70 to 75° C. with mixing at 500 rpm. Component 5 and 6 were added and mixed at 500 rpm until dispersed for about 15 to 25 minutes. At 70 to 75° C., components 7 through 11 were added with mixing.

After cooling the resultant mixture to about 63 to 67° C., elubiol, salicylic acid (component 6) and component 14 were added sequentially thereto with mixing until the latter three components were completely dispersed. The resultant primary mixture was then cooled to 50° C.

Components 15, 16, 21 and 22 were combined in a separate beaker at 25–30° C. to form a premixture. After cooling the primary mixture to 50° C., components 14, 17 and 18 were added. The premixture followed by components 19, 20 and 23 were added thereto sequentially with mixing. Sodium hydroxide was added thereto with mixing to adjust the pH to about 5.3–5.7. The mixture was continuously mixed and cooled to about 25–30° C. The remaining amount of deionized water was added to the final volume and was mixed at 500 rpm until uniform.

Example 3

Preparation of Cleansing Shampoo Containing Two Cationic Agents and One Silicone Quaternary Compound Shampoo comprised of the following components as set forth in Table 3 were prepared:

Example 4

Preparation of Cleansing Shampoo Containing Three Cationic Additives and Two Silicone Quaternary Compounds Shampoos comprised of the following components as set forth in Table 4 were prepared:

TABLE 3

Cleansing shampoo with two cationic deposition enhancing agents and a silicone compound.

| | Trade Name | CTFA | % wt/wt | Supplier |
|---|---|---|---|---|
| 1 | DI water | DI water | 72.765 | |
| 2 | Salcare SC 60 | Acrylamidopropyltrimoniumchloride Acrylamide Copolymer | 0.08 | Ciba Industries |
| 3 | Jaguar C 17 | Guar Hydroxypropyl Trimonium Chloride | 0.15 | Rhone-Poulenc |
| 4 | Citric Acid Anh | Citric Acid | 0.025 | |
| 5 | Cutina AGS | Glycol Distearate | 1.75 | Henkel Corporation |
| 6 | Methyl Paraben | Methyl Paraben | 0.20 | Nipa Hardwicke Inc |
| 7 | Empicol EAC 70 | Ammonium Laureth Sulfate | 3.6 | Albright & Wilson |
| 8 | Empicol AL 70 | Ammonium Lauryl Sulfate | 11.8 | Albright & Wilson |
| 9 | Tego Betaine E | Cocamidopropyl Betaine | 2.43 | Goldschmidt |
| 10 | Tego Betaine F 50 | Cocamidopropyl Betaine | 3.00 | Goldschmidt |
| 11 | Elubiol | Dichlorohenyl Imidazoldioxolan | 0.50 | Janssen Pharm. |
| 12 | Salicylic Acid | Salicylic Acid | 1.00 | Rhone-Poulenc |
| 13 | Polyox WSR-205 | PEG 14M | 0.05 | Amerchol |
| 14 | Ninol LMP | Lauramide MEA | 1.00 | Stepan |
| 15 | DL-Panthenol-50% | Panthenol | 0.15 | Roche |
| 16 | Phytantriol | Phytantriol | 0.025 | Roche |
| 17 | Biosil Basics SPQ | Silicone Quaternium-13 | 0.20 | Biosil |
| 18 | Hydrotriticum WAA | Wheat Amino Acid | 0.22 | Croda |
| 19 | Sodium Benzoate | Sodium Benzoate | 0.20 | EM Industries |
| 20 | Versene 100XL | Tetrasodium EDTA | 0.20 | Dow Chemical |
| 21 | BHT | Butylated Hydroxytoluene | 0.10 | EM Industries |
| 22 | Lorena | Fragrance | 0.50 | Creation Aromatiques |
| 23 | Glycacil L | Iodopropynyl butylcarbamate | 0.05 | Lonza |
| 24 | NaOH (25%) | Sodium Hydroxide | QS | Mallinckrodt |
| | Total | | 100.00 | |

TABLE 4

Cleansing shampoo with three cationic deposition enhancing agents and two silicone compounds.

| | Trade Name | CTFA | % wt/wt | Supplier |
|---|---|---|---|---|
| 1 | DI water | DI water | 72.32 | |
| 2 | Salcare SC 60 | Acrylamidopropylitrimoniumchloride Acrylamide Copolymer | 0.08 | Ciba Specialty |
| 3 | Jaguar C 17 | Guar Hydroxypropyl Trimonium Chloride | 0.15 | Rhone-Poulenc |
| 4 | Citric Acid Anh | Citric Acid | 0.025 | |
| 5 | Cutina AGS | Glycol Distearate | 1.75 | Henkel Corporation |
| 6 | Methyl Paraben | Methyl Paraben | 0.20 | Nipa Hardwicke Inc. |
| 7 | Merquat 2001 | Polyquaternium 47 | 0.30 | Calgon |
| 8 | Empicol EAC 70 | Ammonium Laureth Sulfate | 3.60 | Albright & Wilson |
| 9 | Empicol AL 70 | Ammonium Lauryl Sulfate | 11.8 | Albright & Wilson |
| 10 | Tego Betaine E | Cocamidopropyl Betaine | 2.43 | Goldschmidt |
| 11 | Tego Betaine F 50 | Cocamidopropyl Betaine | 3.00 | Goldschmidt |
| 12 | Elubiol | Dichlorohenyl Imidazoldioxolan | 0.50 | Janssen Pharm. |
| 13 | Salicylic Acid | Salicylic Acid | 1.00 | Rhone-Poulenc |
| 14 | Polyox WSR-205 | PEG 14M | 0.05 | Amerchol |
| 15 | Ninol LMP | Lauramide MEA | 1.00 | Stepan |
| 16 | Biosil Basics SPQ | Silicone Quaternium-13 | 0.20 | Biosil Technologies Inc. |
| 17 | Biosil Basics Cetylsil | Cetyl Triethylmonium-Dimethicone Copolyol Phthalate | 0.15 | Biosil Technologies Inc. |
| 18 | DL-Panthenol-50% | Panthenol | 0.15 | Roche |
| 19 | Phytantriol | Phytantriol | 0.025 | Roche |
| 20 | Hydrotriticum WAA | Wheat Amino Acid | 0.22 | Croda |
| 21 | Sodium Benzoate | Sodium Benzoate | 0.20 | EM Industries |
| 22 | Versene 100XL | Tetrasodium EDTA | 0.20 | Dow Chemical |
| 23 | BHT | Butylated Hydroxytoluene | 0.10 | EM Industries |
| 24 | Lorena | Fragrance | 0.50 | Creation Aromatiques |
| 25 | Glycacil L | Iodopropynyl butylcarbamate | 0.05 | Lonza |
| 26 | NaOH (25%) | Sodium Hydroxide | QS | Mallinckrodt |
| | Total | | 100.00 | |

Shampoo Process

A vessel was charged with ¾ amount of deionized water (component 1). Components 2, 3 and 4 were added sequentially, with ten minute intervals between the additions and with mixing at 500 rpm under constant conditions. The resulting mixture was then heated to about 70 to 75° C. with mixing at 500 rpm. Component 5 and 6 were added thereto and mixed at 500 rpm until dispersed, i.e., for about 15 to 25 minutes. At 70 to 75° C., components 7 through 11 were added thereto with mixing.

After cooling the resultant mixture to about 63 to 67° C., elubiol, salicylic acid (component 13) and component 14 were added sequentially thereto with mixing until the latter three components were completely dispersed therein. The resultant primary mixture was then cooled to 50° C.

Components 18, 19, 23 and 24 were combined in a separate beaker at 25–30° C. to form a premixture. After cooling the primary mixture to 50° C., components 15, 16, 17 and 20 were added thereto. The premixture followed by components 21, 22 and 25 added thereto sequentially with mixing. Sodium hydroxide was then added thereto with mixing to adjust the pH to about 5.3–5.. The mixture was continuously mixed and cooled to about 25–30° C. The remaining amount of deionized water was added to the final volume and was mixed at 500 rpm until uniform.

Example 5

Preparation of Cleansing Shampoo Containing Three Cationic Additives and One Silicone Quaternary Compounds Shampoos comprised of the following components as set forth in Table 5 were prepared:

TABLE 5

Cleansing shampoo with three cationic deposition enhancing agents and one silicon compound.

| | Trade Name | CTFA | % wt/wt | Supplier |
|---|---|---|---|---|
| 1 | DI water | DI water | 72.82 | |
| 2 | Salcare SC 60 | Acrylamidopropylitrimoniumchloride Acrylamide Copolymer | 0.08 | Ciba Specialties |
| 3 | Jaguar C17 | Guar Hydroxypropyl Trimonium Chloride | 0.15 | Rhone-Poulenc |
| 4 | Citric Acid Anh | Citric Acid | 0.025 | Roche |
| 5 | Cutina AGS | Glycol Distearate | 1.75 | Henkel Corporation |
| 6 | Methyl Paraben | Methyl Paraben | 0.20 | Nipa Hardwicke Inc. |
| 7 | Empicol EAC 70 | Ammonium Laureth Sulfate | 3.6 | Albright & Wilson |
| 8 | Empicol AL 70 | Ammonium Lauryl Sulfate | 11.8 | Albright & Wilson |

TABLE 5-continued

Cleansing shampoo with three cationic deposition enhancing agents and one silicon compound.

| | Trade Name | CTFA | % wt/wt | Supplier |
|---|---|---|---|---|
| 9 | Tego Betaine E | Cocamidopropyl Betaine | 2.43 | Goldschmidt |
| 10 | Tego Betaine F 50 | Cocamidopropyl Betaine | 3.00 | Goldschmidt |
| 11 | Elubiol | Dichlorophenyl Imidazoldioxolan | 0.500 | Janssen Pharm. |
| 12 | Salicylic Acid | Salicylic Acid | 1.000 | Rhone-Poulenc |
| 13 | Polyox WSR-205 | PEG 14M | 0.05 | Amerchol |
| 14 | Ninol LMP | Lauramide MEA | 1.00 | Stepan |
| 15 | Biosil Basics Cetylsil | Cetyl Triethylmonium-Dimethicone Copolyol Phthalate | 0.15 | Biosil Technologies Inc. |
| 16 | Hydrotriticum WAA | Wheat Amino Acid | 0.220 | Croda |
| 17 | DL-Panthenol-50% | Panthenol | 0.15 | Roche |
| 18 | Phytantriol | Phytantriol | 0.025 | Roche |
| 19 | Sodium Benzoate | Sodium Benzoate | 0.20 | EM Industries |
| 20 | Versene 100XL | Tetrasodium EDTA | 0.20 | Dow Chemical |
| 21 | BHT | Butylated Hydroxytoluene | 0.10 | EM Industries |
| 22 | Lorena | Fragrance | 0.50 | Creation Aromatiques |
| 23 | Glycacil L | Iodopropynyl butylcarbamate | 0.05 | Lonza |
| 24 | Citric Acid | Citric Acid (50%) | QS | Mallinckrodt |
| | Total | | 100.00 | |

Shampoo Process

A vessel was charged with ¾ amount of deionized water (component 1). Components 2, 3 and 4 were added sequentially, with ten minute intervals between the additions and with mixing at 500 rpm under constant conditions. The resulting mixture was then heated to 70 to 75° C. with mixing at 500 rpm. Components 5 and 6 were then to the mixture with mixing for about 15 to 25 minutes. The resultant mixture was maintained at 70–75° C., and components 7 through 10 were sequentially added thereto with mixing.

After the resultant mixture was cooled to about 63–67° C., elubiol (component 11) was added thereto with mixing under constant conditions. Salicylic acid was then added thereto followed by component 13 under constant mixing to form a primary mixture.

Components 15, 16, 21 and 22 were combined in a separate beaker at 25–30° C. to form a premixture. After cooling the primary mixture to 50° C., components 14, 17, and 18 were sequentially added thereto with mixing. The premixture was then added thereto. Sodium hydroxide was then added thereto with mixing to adjust the pH to about 5.3–5.7. The mixture was continuously mixed and cooled to about 25–30° C. The remaining amount of deionized water was added to the final volume and was mixed at 500 rpm until uniform.

Example 6

Preparation of Cleansing Shampoo

Shampoos comprised of the following components as set forth in Table 6 were prepared:

TABLE 6

Cleansing shampoo.

| | Trade Name | CTFA | % wt/wt | Supplier |
|---|---|---|---|---|
| 1 | DI water | DI water | 72.225 | |
| 2 | Cutina AGS | Glycol Distearate | 1.75 | Henkel Corporation |
| 3 | Methyl Paraben | Methyl Paraben | 0.20 | Nipa Hardwicke Inc. |
| 4 | Empicol EAC 70 | Ammonium Laureth Sulfate | 3.60 | Albright & Wilson |
| 5 | Empicol AL 70 | Ammonium Lauryl Sulfate | 11.8 | Albright & Wilson |
| 6 | Tego Betaine E | Cocamidopropyl Betaine | 2.43 | Goldschmidt |
| 7 | Tego Betaine F 50 | Cocamidopropyl Betaine | 3.00 | Goldschmidt |
| 8 | Elubiol | Dichlorophenyl Imidazoldioxolan | 0.50 | Janssen Pharm. |
| 9 | Salicylic Acid | Salicylic Acid | 1.00 | Rhone-Poulenc |
| 10 | Polyox WSR-205 | PEG 14M | 0.05 | Amerchol |
| 11 | Ninol LMP | Lauramide MEA | 1.00 | Stepan |
| 12 | Hydrotriticum WAA | Wheat Amino Acid | 0.22 | Croda |
| 13 | DL-Panthenol-50% | Panthenol | 0.15 | Roche |
| 14 | Phytantriol | Phytantriol | 0.025 | Roche |
| 15 | Sodium Benzoate | Sodium Benzoate | 0.20 | EM Industries |
| 16 | Versene 100XL | Tetrasodium EDTA | 0.20 | Dow Chemical |
| 17 | BHT | Butylated Hydroxytoluene | 0.10 | EM Industries |
| 18 | Lorena | Fragrance | 0.50 | Creation Aromatiques |
| 19 | Glycacil L | Iodopropynyl butylcarbamate | 0.05 | Lonza |
| 20 | NaOH | NaOH (25%) | QS | Mallinckrodt |
| | Total | | 100.00 | |

Shampoo Process

A vessel was charged with ¾ amount of deionized water (component 1) and heated to about 70 to 75° C. Components 2 and 3 were added thereto with mixing at 500 rpm under constant conditions for 15 to 20 minutes. Component 4 through 7 were added sequentially thereto with mixing under constant conditions. After the resultant mixture was then cooled to 63–67° C., elubiol (component 11) was added thereto with mixing under constant conditions. Salicylic acid was then added thereto followed by component 10 under constant mixing to form a primary mixture.

Components 13, 14, 17 and 18 were combined in a separate beaker at 25–30° C. to form a premixture. After cooling the primary mixture to 50° C., the premixture was added thereto, then components 15, 16 and 19 were sequentially added thereto with mixing. Sodium hydroxide was then added thereto with mixing to adjust the pH to about 5.3–5.7. The mixture was then continuously mixed and cooled to about 25–30° C. The remaining amount of deionized water was added to the final volume and was mixed at 500 rpm until uniform.

Example 7

Preparation of Cleansing Shampoo Containing One Water Soluble Silicone Compound

Shampoos comprised of the following components as set forth in Table 7 were prepared:

Shampoo Process

A vessel was charged with ¾ amount of deionized water (component 1). Components 2 was then added thereto. The resultant mixture was then heated to 70–75° C., and components 3 & 4 were sequentially added thereto with mixing at 500 rpm under constant conditions. Component 5 through 8 were then sequentially added thereto with mixing under constant conditions. The resulting mixture was cooled to about 63 to 67° C. with mixing at 500 rpm. Component 9 was then added to the mixture. After all the elubiol had dissolved therein, salicylic acid (component 10) was added thereto with mixing for 15–20 minutes at constant conditions; component 11 then was added thereto. The resultant primary mixture was then cooled to 50° C.

Components 13, 14, 19 and 20 were combined in a separate beaker at 25–30° C. to form a premixture. After cooling the primary mixture to 50° C., component 12, component 15, component 16, the premixture, component 17, component 18 and component 21 were sequentially added thereto with mixing. Sodium hydroxide was added thereto with mixing to adjust the pH to about 5.3–5.7. The mixture was continuously mixed and cooled to about 25–30° C. The remaining amount of deionized water was added to the final volume and mixed at 500 rpm until uniform.

TABLE 7

Cleansing shampoo with one water soluble silicone deposition enhancing agents.

| | Trade Name | CTFA | % wt/wt | Supplier |
|---|---|---|---|---|
| 1 | DI water | DI water | 73.00 | |
| 2 | Citric Acid Anh | Citric Acid | 0.025 | Roche |
| 3 | Cutina AGS | Glycol Distearate | 1.75 | Henkel Corporation |
| 4 | Methyl Paraben | Methyl Paraben | 0.20 | Mallinckrodt |
| 5 | Empicol EAC 70 | Ammonium Laureth Sulfate | 3.6 | Albright & Wilson |
| 6 | Empicol AL 70 | Ammonium Lauryl Sulfate | 11.8 | Albright & Wilson |
| 7 | Tego Betaine E | Cocamidopropyl Betaine | 2.43 | Goldschmidt |
| 8 | Tego Betaine F 50 | Cocamidopropyl Betaine | 3.00 | Goldschmidt |
| 9 | Elubiol | Dichlorophenyl Imidazoldioxolan | 0.50 | Janssen Pharm. |
| 10 | Salicylic Acid | Salicylic Acid | 1.00 | Rhone-Poulenc |
| 11 | Polyox WSR-205 | PEG 14M | 0.05 | Amerchol |
| 12 | Ninol LMP | Lauramide MEA | 1.00 | Stephan |
| 13 | DL-Panthenol-50% | Panthenol | 0.15 | Roche |
| 14 | Phytantriol | Phytantriol | 0.025 | Roche |
| 15 | Biosil Basic SPQ | Silicone Quaternium 13 | 0.20 | Biosil |
| 16 | Hydrotriticum WAA | Wheat Amino Acid | 0.22 | Croda |
| 17 | Sodium Benzoate | Sodium Benzoate | 0.20 | EM Industries |
| 18 | Versene 100XL | Tetrasodium EDTA | 0.20 | Dow Chemical |
| 19 | BHT | Butylated Hydroxytoluene | 0.10 | EM Industries |
| 20 | Lorena | Fragrance | 0.50 | Creation Aromatiques |
| 21 | Glycacil L | Iodopropynyl butylcarbamate | 0.05 | Lonza |
| 22 | NaOH (25%) | Sodium Hydroxide | QS | Mallinckrodt |
| | Total | | 100.00 | |

Example 8

Preparation of Cleansing Shampoo Containing Two Water Soluble Silicone Compounds Shampoos comprised of the following components as set forth in Table 8 were prepared:

creaminess of the lather). The four formulations tested in this study included: 1) the formulation prepared in accordance with Example 3; 2) "Pantene Pro-V" regular shampoo for normal hair commercially available from Procter & Gamble; 3) "Johnson's pH 5.5" regular shampoo for normal hair commercially available from Johnson & Johnson Con-

TABLE 8

Cleansing shampoo with two water soluble silicone deposition enhancing agents.

| | Trade Name | CTFA | % wt/wt | Supplier |
|---|---|---|---|---|
| 1 | DI water | DI water | 73.00 | |
| 2 | Citric Acid Anh | Citric Acid | 0.025 | Roche |
| 3 | Cutina AGS | Glycol Distearate | 1.75 | Henkel |
| 4 | Methyl Paraben | Methyl Paraben | 0.20 | |
| 5 | Empicol EAC 70 | Ammonium Laureth Sulfate | 3.6 | Albright & Wilson |
| 6 | Empicol AL 70 | Ammonium Lauryl Sulfate | 11.8 | Albright & Wilson |
| 7 | Tego Betaine E | Cocamidopropyl Betaine | 2.43 | Goldschmidt |
| 8 | Tego Betaine F 50 | Cocamidopropyl Betaine | 3.00 | Goldschmidt |
| 9 | Elubiol | Dichlorophenyl Imidazoldioxolan | 0.50 | Janssen Pharm. |
| 10 | Salicylic Acid | Salicylic Acid | 1.00 | Rhone-Poulenc |
| 11 | Polyox WSR-205 | PEG 14M | 0.05 | Amerchol |
| 12 | Ninol LMP | Lauramide MEA | 1.00 | Stephan |
| 13 | DL-Panthenol-50% | Panthenol | 0.15 | Roche |
| 14 | Phytantriol | Phytantriol | 0.025 | Roche |
| 15 | Biosil Basic SPQ | Silicone Quaternium 13 | 0.20 | Biosil |
| 16 | Biosil Basic Cetylsil | Cetyl Triethylammonium Dimethicone Copolyol Phthalate | 0.15 | Biosil |
| 17 | Hydrotriticum WAA | Wheat Amino Acid | 0.22 | Croda |
| 18 | Sodium Benzoate | Sodium Benzoate | 0.20 | EM Industries |
| 19 | Versene 100XL | Tetrasodium EDTA | 0.20 | Dow Chemical |
| 20 | BHT | Butylated Hydroxytoluene | 0.10 | EM Industries |
| 21 | Lorena | Fragrance | 0.50 | Creation Aromatiques |
| 22 | Glycacil L | Iodopropynyl butylcarbamate | 0.05 | Lonza |
| 23 | NaOH (25%) | Sodium Hydroxide | QS | Mallinckrodt |
| | Total | | 100.00 | |

Shampoo Process

A vessel was charged with a amount of deionized water (component 1). Components 2 was then added thereto. The resultant mixture was then heated to 70–75° C. and components 3 and 4 were sequentially added thereto with mixing at 500 rpm under constant conditions. Component 5 through 8 were sequentially added thereto with mixing under constant conditions. After cooling the resulting mixture to about 63 to 67° C. with mixing at 500 rpm, component 9 was then added to the mixture. After all the elubiol had dissolved therein, salicylic acid (component 10) was added thereto with mixing for 15–20 minutes at constant conditions; component 11 was then added thereto. The resultant primary mixture was then cooled to 50° C.

Components 13, 14, 20 and 21 were combined in a separate beaker at 25–30° C. to form a premixture. After cooling the primary mixture to 50° C., component 12, component 15, component 16, component 17 the premixture, component 18, component 19 and component 22 were sequentially added thereto with mixing. Sodium hydroxide was then added thereto with mixing to adjust the pH to about 5.3–5.7. The mixture was continuously mixed and cooled to about 25–30° C. The remaining amount of deionized water was added to the final volume and was mixed at 500 rpm until uniform.

Example 9

Multiple Attribute Assessment Study

A large-scale consumer study was conducted to assess a variety of attributes such as cleansing ability; hair combing attributes (e.g. wet combing and dry combing); hair softness: and lather attributes (e.g. the amount of lather and the sumer Companies, Inc.; and 4) "Johnson's pH 5.5" regular shampoo modified with a different fragrance.

For each of the four above-mentioned test products, 250 female subjects between the age of 16–65 who use regular shampoos for normal hair were selected to participate in a blinded, monadic in-home use study. After using the test product for 2 weeks, each subject completed a questionnaire which asked them to rate the overall performance of the test product as well as and various attributes associated therewith.

The following table is a summary of the results from study:

TABLE 9

% of subjects satisfied with the performance of the product in each attribute listed.

| Attributes | pH 5.5 (a) | pH 5.5 with modified fragrance (b) | Example #3 (base w/2 cationic agents & 1 silicone agent) (c) | Pantene (e) |
|---|---|---|---|---|
| Cleaning | 88% | 86% (4) | 91% (3) | 88% |
| Wet combing | 71% (2) | 66% (2) | 83% (1) (3) | 77% (4) |
| Dry combing | 72% (2) | 78% (2) | 86% (1) | 83% |
| Hair Softness | 78% (2) | 78% (2) | 90% (1) | 86% |
| Amount of lather | 41% | 37% (2) | 47% (1) (3) | 38% (4) |
| Creaminess of lather (Very creamy) | 14% (2) | 11% (2) | 27% (1) (3) | 21% (4) |

(1): formulations identified with a "(1)" are significantly higher than those formulations identified with a "(2)" at 95% two tailed level of confidence;
(3): formulations identified with a "(3)" are significantly higher than those formulations identified with a "(4)" at 80% two tail level of confidence This Example showed that the formulation of Example 3 ranked superior with respect to the subject's satisfaction in all the attributes listed above. More specifically, the formulation of Example 3 performed significantly better relative to the performance of the pH 5.5 product with either the original and modified fragrance with respect to the following attributes: wet combing, dry combing, hair softness, cleansing, amount of lather and creaminess of the lather. The formulation of Example 3 also performed significantly superior relative to the performance of Pantene with respect to wet combing, amount of lather and creaminess of the lather. This Example showed that the subjects perceived that the formulation of Example 3 performed the best overall with respect to the attributes tested.

Example 10

Hair Softness Assessment

80 Caucasian females between the ages of 18 and 65 years old were selected to participate in a blind hair softness assessment study conducted by professional hair stylists. Prior to participating in the study, each subject did not wash their hair for a period of 24 hours prior to the study entry. All of the subjects as well as the stylist completed two different questionnaires relating to the hair quality and hair softness of each panelist before the study commenced.

The following three methods were used for purposes of assessing hair softness: 1) pat and compress hair with hands; 2) run fingers through the hair; and 3) feel the hair fibers/strands with fingers.

After 3 cc of the formulation of Example 3 was applied via a syringe onto the hair on each respective subject's head, the stylist then shampooed the hair of each respective subject. After this procedure was repeated twice per subject, the hair of each subject was then blown until the hair was completely dried. No other styling aides were used on hair or scalp of any of the subjects. After the drying procedure both the respective subject as well as the stylist conducted an independent evaluation of the respective subject's hair softness, using the Softness scale as set forth in Table 10 below. The results of the evaluations are set forth in Table 11 below.

TABLE 10

Softness Scale

| Number Score | Softness Assessment |
| --- | --- |
| 0 | Not At all Soft |
| 1 | Just Barely Soft |
| 2 | Between Just Barely and Slightly Soft |
| 3 | Slightly Soft |
| 4 | Slightly to Moderately Soft |
| 5 | Moderately Soft |
| 6 | Moderately to Considerably Soft |
| 7 | Considerable Soft |
| 8 | Considerably to Very Soft |
| 9 | Very soft |
| 10 | Extremely Soft |

TABLE 11

Softness assessments determine by the subject and stylist.
The numbers represent the mean score from 80 subjects.

| Evaluator | Pre-wash softness score | Post-Wash Score | p-value |
| --- | --- | --- | --- |
| Stylist | 2.74 | 7.44 | 0.0001 |
| Subject | 3.50 | 7.58 | 0.0001 |

It is evident from the data above that the formulation of Example 3 significantly increased the softness of the hair as determined independently by the stylist and the subjects.

Each respective subject as well as the stylist also conducted an independent, post-drying evalution of the degree of softness of each respective subject's hair, using the Hair Softness Quantification Scale as set forth in Table 12 below. The results of the evaluations are set forth in Table 13 below.

TABLE 12

Hair Softness Qualification Scale

| Number Scale | Distinction |
| --- | --- |
| −1 | Less Soft |
| 0 | The Same |
| 1 | Somewhat Softer |
| 2 | Twice as soft |
| 3 | Three times as soft |
| 4 | More than Three times as soft |

TABLE 13

Qualification of the hair softness.
The numbers below represent mean score values from 80 subjects.

| Evaluator | Mean Times Softer Score | p-value |
| --- | --- | --- |
| Stylist | 2.44 | 0.0001 |
| Subject | 2.33 | 0.0001 |

From the data above, it is evident that the formulation of Example 3 was approximately two to three times more soft as a result of shampooing with this cleansing base.

Example 11

Secondary Ion Mass Spectrometry (SIMS) to Assess Si Deposition

A formulation was prepared in accordance with the procedure set forth in Example 3, except that: a) the Biosil SPQ silicone agent was used instead at a concentration of 1 weight percent as opposed to 0.2 weight percent; b) the Salcare cationic agent was used instead at a concentration of 0.05 weight percent as opposed to 0.08 weight percent; and c) the Jaguar cationic agent was used instead at a concentration of 0.1 weight percent as opposed to 0.15 weight percent.

One hair tress was independently washed five times, followed by complete drying of the tress in between washings, with Pantene Pro-V 2-in-1 shampoo for normal hair that is commercially available from The Procter and Gamble Company, and another hair tress was similarly washed with the formulation of Example 3 as modified in Example 11 and dried.

Scanning SIMS (secondary ion mass spectrometry) was then used to characterize the distribution of silicone ions from the silicone-containing polymers that were deposited on the hair. Details of SIMS may be found in, for example, Sibilia, John, "A Guide to Material Characterization and Chemical Analysis," Ch. 8, 185–192 (1988)(hereinafter "Sibilia"), which is incorporated by reference herein. After placing one fiber of each tress in a Physical Electronics SIMS spectrometer, a primary ion beam was then scanned across the hair surface in order to ionize the Si molecules from the hair surface. The spectrometer then generated images revealing the distribution of Si ions on the surface of the hair.

This procedure was repeated with several hair fibers from each tress, and representative mass spectrometer images were taken of each set of hair fibers.

Figure 1B:
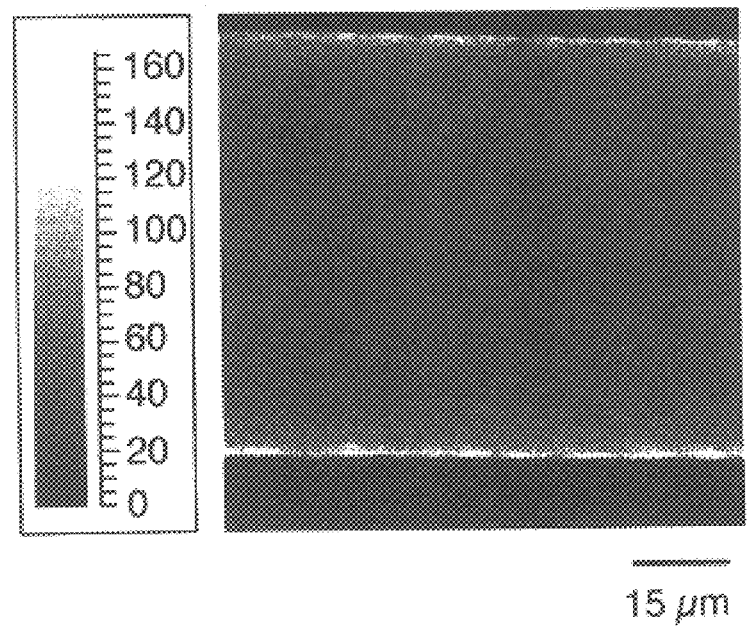

It is evident from FIG. 1, which illustrates the distribution of Si ions on the hair surface that was washed with the Pantene Pro-V shampoo, that the Si ions were distributed over the surface hair fiber; however, the Ions were primarily concentrated only under the scale ridge of the hair fiber. By contrast, it is event from FIG. 2, which illustrates the distribution of Si ions on the hair surface that was washed with the modified Example 3 formulation, that the distribution of the Si ions is comparatively more homogenous than the distribution shown by the hair fibers washed with the Pantene Pro-V shampoo.

This Example showed that the cleansing composition of the present invention yielded a more homogeneous distribution of the Silicone polymers, which thereby significantly contributed to the improved softness and body of the treated hair fibers.

Example 12

X-Ray Photoelectron Spectrometer (XPS) to Assess Polymer Thickness

After each tress of Example 11 was placed into a Physical Electronics ray photoelectron spectrometer, a beam of X-rays were scanned onto the surface of the hair fibers. Details of XPS may be found in, for example, Sibilia at 197–199, which is incorporated by reference herein.

From the percentage of Carbon and Oxygen atoms on the hair fiber and the atomic ratios of Si:C and Si:O as determined by XPS, the thickness of the silicone polymer layer on the hair surface was estimated as shown in Table 14 below:

TABLE 14

Thickness of Silicone molecules on the hair as determined by XPS.

| Formulation | Thickness of Si molecules (Angstroms) | Number of monolayers |
|---|---|---|
| Pantene Pro-V | 40–50 | 7–8 |
| Modified Example 3 | 3 | 1 |

It is evident from the results of Table 14 that the Pantene shampoo left substantially higher levels of silicon molecular residue on the hair surface in comparison to the amount of such residue left by the modified Example 3 formulation. We believe that the higher levels of silicon deposition along the hair surface may contribute to the perception of high conditioning build-up on the hair, reduction in body, and limpness. By contrast, since the hair treated with the modified Example 3 formulation left only one or two layers of silicon molecular residue on the surface of the hair fibers, we believe that hair treated with this formulation will likely possess attributes, such as enhanced wet and dry comb, improved rinsing performance and enhanced softness, that are superior relative to such properties possessed by hair treated with the Pantene shampoo.

Since the performance of a hair care product largely depends upon on how the product interacts with the outermost layer of the hair fiber, this example indicated that the modified Example 3 shampoo will have a superior performance relative to that of the Pantene shampoo based upon a chemical and elemental analysis of the respective shampoo's residue left at the interface between the hair surface and the air.

Example 13

Instron Ring Compression Study to Assess Hair Softness and Body

The ring compression technique, which measures the energy require to pull hair tresses through various sized rings both before and after the tresses are shampooed, is a well known technique as described in Wergmann & Kamuth, *Principles of Polymer Science and Technology in Cosmetics and Personal Care,* Chapter 12 "Evaluation Methods for Conditioned Hair" 554–556 (1999), which is incorporated herein by reference, for assessing hair softness and body. See, e.g., Garcia et al, "Measurement of Bulk Compressibility and Bulk Resiliency of a Hair Mass," $10^{th}$ IFTSCC Congress, Sidney, Australia (1978), which is incorporated by reference herein. The apparatus used in this technique consisted of an Instron tensile tester, model 1122, which is connected to ring devices of varying diameters.

After 15 brown European hair tresses were permed with a tight perm, each tress was pulled through a metal ring having a 1.5" inner diameter twice. The energy required to pull the tress through the ring was then recorded via the Instron tester. The tresses were then manually loosened and pulled through a second metal ring having a 1.0" inner diameter twice. The energy required to pull the tress through this second ring was then recorded via the Instron tester.

The "Dry Pull Energy" required to pull a tress through a given ring may be expressed in terms of the difference between the energy exerted to pull a tress through the same ring twice. This value is a measure of the degree of body or rebound of the hair tress after compression. Higher values of Dry Pull Energy indicate greater hair body.

The difference between the Dry Pull Energies required to pull each tress through the 1.0" and the 1.5" diameter rings, respectively, is an indication of the softness of the hair tress. The greater the difference between the difference in the Dry Pull Energies indicates that the respective hair tress is relatively more compressible or softer. The difference in the Dry Pull Energies resulting the tress being pulled through a 1.0" inch ring and then through a 1.5" inch diameter ring are shown in Table 15 and 16 below for the dry permed hair.

The tresses were then shampooed once with one of the following products: 1) the formulation of Example 3; 2) "Pantene Pro-V" shampoo for normal hair; and 3) "Shiseido Super Mild" shampoo commercially available from Shiseido Fine Toiletries Co., LTD. A minimum of 3 tresses was used for each product. After the tresses were shampooed and blown completely dry, the tresses were manually loosened to separate the individual hair fibers. The tresses were then pulled through the rings in accordance with the procedures as described above.

The difference in the Dry Pull Energies resulting from the tress being pulled through the same size ring twice, i.e. a 1.0" diameter ring and independently a 1.5" diameter ring, both before the hair is shampooed as well as after the hair is both shampooed and dried are shown in the Table 17 below.

TABLE 15

Dry Pull Energy (mJ)

| Test Product | Dry Pull Energy Before Shampooing | Dry Pull Energy After Shampooing | Difference Between Dry Pull Energy Before and After treatments |
|---|---|---|---|
| Example 3 | 16.0 | 10.0 | 6.0 |
| Pantene Pro V | 20.3 | 16.8 | 3.5 |
| Shiseido Super Mild | 7.99 | 7.90 | 0.09 |

TABLE 16

Statistical significance of represented by p-values determined by the Student's t-test*.

| Formulations | p-value |
|---|---|
| Example 3 vs. Pantene | >0.000 |
| Example 3 vs. Shiseido | 0.026 |

It is evident from the data above that the formulation of Example 3 showed the greatest difference in Dry Pull Energies, which indicates that this formulation is superior with respect to the other two tested commercial formulations with respect to delivering softness to the hair fibers.

TABLE 17

Dry Pull Energy (mJ)

| Test Product | Dry Pull Energy Before shampooing Pulled through 1.0" Ring | Dry Pull Energy After Shampooing Pulled through 1.0" Ring | Difference between Dry Pull Energies before and after shampooing (1.0" ring) | Dry Pull Energy Before shampooing Pulled through 1.5" Ring | Dry Pull Energy After Shampooing Pulled through 1.5" Ring | Difference between Dry Pull Energies Before and After Shampooing (1.5" ring) |
|---|---|---|---|---|---|---|
| Example 3 | 2.76 | 1.31 | 1.45 | 2.20 | 1.07 | 1.13 |
| Pantene Pro V | 2.39 | 1.56 | 0.83 | 2.19 | 1.43 | 0.76 |
| Shiseido Super Mild | 1.26 | 1.05 | 0.21 | 1.34 | 0.93 | 0.41 |

It is evident from the data in Table 17 above that the formulation of Example 3 showed the greatest difference in Dry Pull Energy before and after shampooing regardless of the ring size employed. This indicates that the formulation of Example 3 exhibited the greatest amount of body and/or rebound relative to that possessed by the other two commercial products.

Example 14

Dynamic Vapor Sorption Studies to Determine Moisture Uptake

Dynamic Vapor Sorption (DVS), Surface Measurement Systems, Ltd., was used to determine the water absorption and moisture desorption on hair fibers after application of a composition thereto.

Four hair tresses were individually shampooed twice with 3 g of one of the formulations prepared in accordance with one of the following examples as shown in Table 18 below: 1) modified Example 3; 2) Example 6; 3) modified Example 7: and 4) modified Example 6. After blow drying the hair tresses for 2 minutes, the tresses were then cut into segments 5–7 mm in length and weighed using a DVS Cain microbalance. The weights of the hair samples ranged between approximately 30 mg to 40 mg/sample. The hair samples were then placed into the DVS humidity chamber and equilibrated at 0% relative humidity at 25° C. overnight. The relative humidity in the chamber was then increased to 10% RH until equilibration occurred. The relative humidity was then increased to 95% RH in approximately 10% RH intervals. The weight of the hair samples was then measured at each interval after each equilibration using the Cain microbalance. The relative humidity was then reduced back to 10% RH in ~10% RH intervals. The weight of the hair fibers at each 10% RH interval is an indication of the water moisture absorbed and of the moisture retained by the hair samples. The water retaining capacity is the difference between the measured weight of water retained by the hair fibers at a given relative humidity during the ascent of the relative humidity versus measured weight of water retained by the hair fibers at a given relative humidity during the descent of the relative humidity. Higher values of water retaining capacity indicate the presence of surface water on the hair fiber, which tends to create limpness of the hair or increase interfiber adhesion. Lower values water retaining capacity indicated the reduction of water by the hair fiber, which tend to increase the body of the hair. A summary of the water retaining capacities is shown in Table 19 below.

TABLE 18

Summary of formulations tested and modifications.

| Formulations | Number of Cationic | Number of Silicones | Modifications in Formulation |
|---|---|---|---|
| Modified Example 3 | 2 | 1 | Jaguar is 0.10 wt % instead of 0.15 wt % |
| Example 6 | 0 | 0 | No modifications |
| Modified Example 7 | 0 | 1 | No PEG 14M |
| Modified Example 6 | 0 | 0 | No PEG 14M |

TABLE 19

Water Retaining Capacities

| Test Products | Moderate Relative Humidity (calculated at 60% RH) | High Relative Humidity (calculated at 80% RH) |
|---|---|---|
| Untreated | 2.34 | 1.80 |
| Modified example 3 | 2.14 | 1.65 |
| Example 8 | 2.53 | 1.88 |
| Modified Example 7 | 2.34 | 1.82 |
| Modified example 6 | 2.47 | 1.99 |

It is evident from the data above that the formulation of Example 3 as modified above in Table 18 possessed superior body properties at both moderate and high relative humidity conditions. By contrast, the formulations that did not contain a cationic agent and/or a silicone agent did not perform relatively as well. This Example showed that formulations exhibiting superior body preferably contain both at least two cationic agents as well as one silicone agent.

Example 15

Determination of Skin Permeation

Experiments were conducted to determine the deposition of actives into the skin from various shampoo compositions. To determine penetration of actives, in vitro skin permeation studies were conducted using non-occluded Franz diffusion chambers.

Human cadaver skin, microtomed to 400 $\mu$m, were mounted on Franz diffusion cells containing a receptor medium composed of a citric acid phosphate buffer or a phosphate buffered solution (depending on the active being monitored). The receptor capacity was 5 ml and the cell surface was 0.636 cm$^2$. The receptor compartment was maintained at 37° C. during the experiment.

In a tube, 50 $\mu$l of each formulation as shown in Tables 1 and 2 through 6 were diluted with 50 $\mu$l of 37° C. water. This solution was then rubbed onto the epidermal surface of the mounted skin for 30 seconds and allowed to sit thereon for 5 minutes. The solution was then rinsed from the surface three times with 37° C. water, and then swabbed twice with dry cotton swabs. At 24 hours after the topical application of the formulation, the surface of the skin was rinsed three times with methanol or distilled water soaked cotton swabs (depending on the active to be monitored), and then swabbed three times wig three dry cotton swabs. After removing the skin from the diffusion cell, the epidermis and dermis were separated, chopped and placed into separate vials containing an extraction solution and sonicated in a bath sonicator for 30 minutes. After sonication of the epidermis, dermis and swabs, respectively, each sonicated sample was assayed using a Walters high pressure liquid chromatography ("HPLC"). Penetration of the active into the skin was calculated based upon a percentage of the applied dose and the amount of active delivered into the epidermis or dermis per surface area. For these studies, the penetration of a lipophilic agent, elubiol was investigated. Also the penetration of a hydrophilic agent, salicic acid was investigated.

As shown in Table 20 below, the formulations investigated were the formulations prepared in accordance with the procedures set forth in Example 1, and Examples 3 through 8. Table 21 shows the amount of elubiol penetrated into the skin (epidermis and dermis) after topical application of the a formulations set forth in Table 20 in accordance with the procedure set forth above.

TABLE 20

Summary of Depositing Agents in each compositions

| Example # | Depositing Agents (Additives) | Number of Cationic | Number of Silicones |
|---|---|---|---|
| 1 | Jaguar, Salcare | 2 | 0 |
| 3 | Jaguar, Salcare, Biosil SPQ | 2 | 1 |
| 4 | Jaguar, Salcare, Merquat, Biosil SPQ, Biosil Cetyl | 3 | 2 |
| 6 | None | 0 | 0 |
| 7 | Biosil Basic SPQ | 0 | 1 |
| 8 | Biosil SPQ, Biosil Cetyl | 0 | 2 |

TABLE 21

Levels of elubiol in the skin (epidermis and dermis) after topical application of various shampoo formulations.

| | Epidermis | | Dermis | | Total Skin Delivery | |
|---|---|---|---|---|---|---|
| Formulations Number tested | Amt/Surface Area ($\mu$g/cm$^2$) | Percentage of Applied Dose % | Amt/Surface Area ($\mu$g/cm$^2$) | Percentage of Applied Dose % | Amt/Surface Area ($\mu$g/cm$^2$) | Percentage of Applied Dose % |
| #1 | 1.849 ± 1.316 | 0.510 ± 0.363 | 0.139 ± 0.058 | 0.038 ± 0.016 | 1.988 | 0.549 |
| #3 | 3.471 ± 2.009 | 1.039 ± 0.601 | 0.173 ± 0.051 | 0.052 ± 0.015 | 3.644 | 1.091 |
| #4 | 8.70 ± 3.35 | 2.433 ± 0.936 | 0.121 ± 0.021 | 0.034 ± 0.006 | 8.822 | 2.466 |
| #6 | 0.412 ± 0.051 | 0.111 ± 0.014 | 0.089 ± 0.023 | 0.024 ± 0.006 | 0.502 | 0.135 |
| #7 | 0.50 ± 0.14 | 0.127 ± 0.036 | 0.398 ± 0.067 | 0.101 ± 0.017 | 0.899 | 0.227 |
| #8 | 0.25 ± 0.02 | 0.064 ± 0.06 | 0.034 ± 0.006 | 0.009 ± 0.002 | 0.279 | 0.072 |

TABLE 22

Statistical significance of elubiol permeation as represented by p-values determined by the Student's test*.

| Formulations | Epidermis | Dermis |
|---|---|---|
| 4 Vs 6 | One Tail = 0.001 | One Tail = 0 |
| | Two Tail = 0.003 | Two Tail = 0 |
| 4 Vs 3 | One Tail = 0.011 | One Tail = 0 |
| | Two Tail = 0.022 | Two Tail = 0 |
| 4 Vs 1 | One Tail = 0.002 | One Tail = 0 |
| | Two Tail = 0.004 | Two Tail = 0 |

*p-values > 0.05 are not significant

The results of Table 21 are summarized below in Table 23.

TABLE 23

Ranking (from best to worst) of the formulations with respect to elubiol delivery into the skin (epidermis and dermis).

| Ranked Example Number | Number of Cationic Agents in Composition | Number Of Silicons in Composition | Total % of Elubiol Delivered into the Skin |
|---|---|---|---|
| 4 | 3 | 2 | 2.466 |
| 3 | 2 | 1 | 1.091 |
| 1 | 2 | 0 | 0.549 |
| 7 | 0 | 1 | 0.227 |
| 6 | 0 | 0 | 0.135 |
| 8 | 0 | 2 | 0.072 |

This Example showed that a formulation (Formulation 4) containing 3 cationic agents and 2 silicones delivered 2.466% of the applied dose of elubiol into the skin. However, when a formulation (Formulation 3) containing 2 cationic agents and 1 silicone were incorporated with the cleansing shampoo base, the percentage of elubiol delivered decreased to 1.091%, over a 2.2 fold decrease in delivery. When no cationic agents were incorporated into the cleansing base (Formulation 6), the elubiol permeation surprisingly decreased to 0.135%, an 18.2 fold decrease over the delivery exhibited by Formulation 4.

It is also evident from this Example that there is a synergistic effect on the permeation of hydrophobic benefit agents in combination with cationic agents and water-soluble silicones. Formulations that contain either a cationic agent alone or a silconeagent alone did not achieve the desired effect of enhanced permeation of the benefit agent. This Example showed that the combination of two or more cationic agents with one or more water soluble silicone agents was superior with respect to permeation of hydrophobic actives into the skin.

The amount of salicylic acid penetrated into the skin (epidermis and dermis) after topical application of the Formulations is set forth in Table 24, wherein the formulations were prepared in accordance with the procedure set forth above.

TABLE 25

Statistical significance of salicylic acid permeation as represented by p-values determined by the Student's t-test*.

| Formulations | Epidermis | Dermis |
|---|---|---|
| 4 Vs. 6 | One Tail = 0.011 | One Tail = 0 |
|  | Two Tail = 0.021 | Two Tail = 0 |
| 4 Vs. 3 | One Tail = 0.373 | One Tail = 0 |
|  | Two Tail = 0.746 | Two Tail = 0 |
| 4 Vs. 1 | One Tail = 0.066 | One Tail = 0 |
|  | Two Tail = 0.132 | Two Tail = 0 |

The results of Table 24 are summarized below in Table 26.

TABLE 26

Ranking (from best to worst) of the formulations with respect to salicylic acid delivery into the skin (epidermis and dermis)..

| Ranking Best to Worst | Number of Cationic Agents | Number Of Silicones | Total % of Salicylic acid Delivered Into the Skin |
|---|---|---|---|
| 4 | 3 | 2 | 1.562 |
| 3 | 2 | 1 | 1.383 |
| 1 | 2 | 0 | 0.700 |
| 6 | 0 | 0 | 0.629 |
| 7 | 0 | 1 | 0.321 |
| 8 | 0 | 2 | 0.121 |

It is evident from Tables 24 and 26 above that Formulation 4, which contained a cleansing base incorporated with three cationic agents and two water-soluble silicones agents (Example 4), delivered the highest levels of salilic acid into the skin. It is further evident that in the formulation containing only silicone agents incorporated with the cleansing base (Example 7 and 8), the level of salicylic acid delivered into the skin was comparatively low. Notably, the cleansing base without the cationic agents and silicone agents (Example 6) possessed superior salicylic acid delivery capabilities in comparison with formulations containing only silicone agents (Example 7 and 8). Formulation 4, which contained both cationic agents and silicone agents, performed 4.9 times better than formulations without cationic

TABLE 24

Levels of salicylic acid in the skin after topical application of various shampoo formulations.

| Formulation Number Tested | Epidermis | | Dermis | | Total Skin Delivery | |
|---|---|---|---|---|---|---|
|  | Amt/Surface Area ($\mu g/cm^2$) | Percentage of Applied Dose % | Amt/Surface Area ($\mu g/cm^2$) | Percentage of Applied Dose % | Amt/Surface Area ($\mu g/cm^2$) | Percentage of Applied Dose % |
| #4 | 11.50 ± 5.07 | 1.508 ± 0.664 | 0.412 ± 0.222 | 0.054 ± 0.029 | 11.912 | 1.562 |
| #6 | 4.83 ± 2.52 | 0.604 ± 0.315 | 0.195 ± 0.141 | 0.024 ± 0.018 | 5.027 | 0.629 |
| #3 | 9.67 ± 5.61 | 1.326 ± 0.769 | 0.419 ± 0.170 | 0.057 ± 0.023 | 10.093 | 1.383 |
| #1 | 5.23 ± 1.27 | 0.675 ± 0.293 | 0.473 ± 0.200 | 0.061 ± 0.026 | 5.707 | 0.700 |
| #7 | 2.36 ± 0.37 | 0.303 ± 0.048 | 0.137 ± 0.028 | 0.018 ± 0.004 | 2.493 | 0.321 |
| #8 | 0.93 ± 0.20 | 0.118 ± 0.025 | 0.022 ± 0.022 | 0.003 ± 0.003 | 0.95 | 0.121 | agents (Example 6) and 1.62 times better than formulations containing only cationic agents (Example 1).

This example demonstrated that the combination of elubiol and salicylic acid in a cleansing shampoo with 2 or more cationic agents and 1 or water soluble silicone agents performed superior with respect to delivering the elubiol and salicylic acid into the skin. Thus, the composition of this invention affords a method of regulating the delivery of both hydrophobic and hydrophilic actives into the skin.

We claim:

1. A cleansing composition, comprising:
   (a) at least one water soluble silicone agent selected from the group consisting of water soluble dimethicones and mixtures of water soluble dimethicones and water soluble silicone quaterniums;
      wherein said water soluble dimethicone is selected from the group consisting of cetyl triethylmonium dimethicone copolyol phthalate, stearalkonium dimethicone copolyol phthalate, dimethicone copolyol acetate, dimethicone copolyol lactate, dimethicone copolyol laurate, dimethicone copolyol methyl ether, dimethicone copolyol octyl dodecyl citrate, hydrolyzed soy protein/dimethicone copolyol acetate and dimethicone copolyols having the following structure:

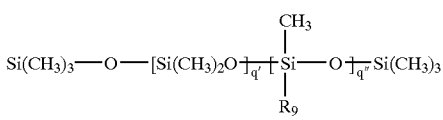

wherein:
   q' is an integer from about 1 to about 7000;
   q" is an integer from about 1 to about 5000;
   $R_9$ is selected from the group consisting of:
      (i) a fatty alcohol having from about 8 carbon atoms to about 30 carbon atoms;
      (ii) a fatty acid having from about 8 carbon atoms to about 30 carbon atoms, and derivatives thereof;
      (iii) a crosslinked water soluble polymer;
      (iv) propyl PG-Betaine; and
      (v) polypeptides
   (b) at least one cationic conditioning agent; and
   (c) at least one detergent comprising about 0.1% to about 30%, by weight, based on the detergent, of at least one anionic surfactant.

2. A cleansing composition, comprising:
   (a) at least one water soluble silicone agent selected from the group consisting of water soluble dimethicones and mixtures of water soluble dimethicones and water soluble silicone quaterniums;
      wherein said water soluble dimethicone is selected from the group consisting of cetyl triethylmonium dimethicone copolyol phthalate, stearalkonium dimethicone copolyol phthalate, dimethicone copolyol acetate, dimethicone copolyol lactate, dimethicone copolyol laurate, dimethicone copolyol methyl ether, dimethicone copolyol octyl dodecyl citrate, hydrolyzed soy protein/dimethicone copolyol acetate and dimethicone copolyols having the following structure:

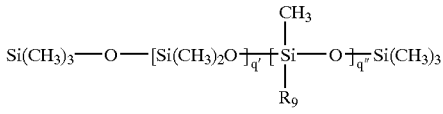

wherein:
   q' is an integer from about 1 to about 7000;
   q" is an integer from about 1 to about 5000;
   $R_9$ is selected from the group consisting of:
      (i) a fatty alcohol having from about 8 carbon atoms to about 30 carbon atoms;
      (ii) a fatty acid having from about 8 carbon atoms to about 30 carbon atoms, and derivatives thereof;
      (iii) a crosslinked water soluble polymer;
      (iv) propyl PG-Betaine; and
      (v) polypeptides
   (b) at least one cationic conditioning agent; and
   (c) at least one detergent comprising about 50% to about 99%, by weight, based on the detergent, of at least one anionic surfactant.

3. The composition of claim 1 or claim 2,
   wherein the dimethicones are substituted with fatty acid moieties selected from fatty acids having from about 5 carbon atoms to about 30 carbon atoms; and
   wherein the silicone quaterniums contain about 6 carbon atoms to about 20 carbon atoms.

4. The composition of claim 1 or claim 2.
   wherein the water soluble silicone agent is said water soluble dimethicone.

5. The composition of claim 1 or claim 2.
   wherein the water soluble silicone quaternium is selected from the group consisting of silicone quaternium 13, silicone quaternium 40, silicone quaternium 80, and mixtures thereof.

6. The composition of claim 1 or claim 2
   wherein the water soluble silicone agent is selected from the group consisting of cetyl triethylmonium dimethicone copolyol phthalate, stearalkonium dimethicone copolyol phthalate, mixtures thereof with silicone quaternium 13, and mixtures thereof.

7. The composition of claim 1 comprising, based upon the total weight of the composition:
   (a) from about 0.001 percent to about 20 percent of water soluble silicone agents;
   (b) from about 0.01 percent to about 10 percent of cationic conditioning agents; and
   (c) from about 0.10 percent to about 30 percent of detergent.

8. The composition of claim 1 comprising, based upon the total weight of the composition:
   (a) from about 0.01 percent to about 5 percent of water soluble silicone agents;
   (b) from about 0.1 percent to about 5 percent of cationic conditioning agents; and
   (c) from about 5 percent to about 20 percent of detergent.

9. The composition of claim 1 or claim 2,
   wherein the cationic conditioning agent is selected from the group consisting of a cationic cellulose derivative; a cationic guar derivative; and a homopolymer or copolymer of a cationic monomer selected from:

a. a monomer having the formula:

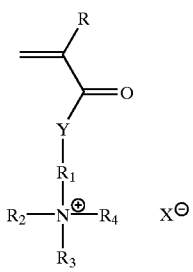

wherein
R is H or $CH_3$,
Y is O or NH,
$R_1$ is an alkylene group having from about 2 to about 6 carbon atoms,
$R_2$, $R_3$ and $R_4$ are each independently an alkyl group or hydroxyalkyl group having from about 1 to about 22 carbon atoms, and
X is a monovalent anion selected from halide and alkyl sulfate having from about 1 to about 4 carbon atoms; and
b. diallyldimethylammonium chloride.

10. The composition of claim 9 wherein the cationic conditioning agent is selected from the group consisting of polyquaternium-10, guar hydroxypropyltrimonium chloride, compounds derived from acrylamidopropyl trimonium chloride/acrylamide copolymer, polyquatermium-6, polyquatermium-7, polyquatermium-47, and mixtures thereof.

11. The composition of claim 10 wherein the cationic conditioning agent is selected from the group consisting of acrylamidopropyltrimonium chloride/acrylamide copolymer, guar hydropropytrimonium chloride, and mixtures thereof.

12. The composition of claim 1 or claim 2,
wherein the detergent is a surfactant, soap, or mixture thereof.

13. The composition of claim 1,
wherein the detergent comprises, based upon the total weight of the detergent:
(a) from about 1 percent to about 20 percent of an anionic surfactant;
(b) from about 1 percent to about 10 percent of an amphoteric surfactant;
(c) from about 0 percent to about 4 percent of a cationic surfactant; and
(d) from about 1 percent to about 7 percent of a nonionic surfactant.

14. The composition of claim 2,
wherein the detergent comprises, based upon the total weight of the detergent:
(a) from about 80 percent to about 95 percent of an anionic surfactant selected from the group consisting of alkyl sulfates, alkyl ether sulfates, and mixtures thereof,
wherein the alkyl groups have from about 8 carbon atoms to about 18 carbon atoms; and
(b) from about 5 percent to about 15 percent of an amphoteric surfactant comprising at least a cocamidopropyl betaine.

15. The composition of claim 2,
wherein the detergent comprises, based upon the total weight of the detergent:
(a) from about 70 percent to about 90 percent of an anionic surfactant selected from the group consisting of sodium PEG-7 olive oil carboxylate, alkyl sulfates, alkyl ether sulfates, and mixtures thereof; wherein the alkyl group has from about 8 carbon atoms to about 18 carbon atoms;
(b) from about 10 percent to about 25 percent of an amphoteric surfactant containing at least a cocamidopropyl betaine; and
(c) from about 2 percent to about 10 percent of a cationic surfactant.

16. The composition of claim 1 or claim 2, further comprising at least one benefit agent.

17. The composition of claim 16 wherein the benefit agent is selected from the group consisting of elubiol, 6-(1-piperidinyl)-2,4-pyrimidinediamine-3-oxide, shale oil and derivatives thereof, finasteride, ketoconazole, salicylic acid, zinc pyrithione, coal tar, benzoyl peroxide, selenium sulfide, hydrocortisone, sulfur, menthol, pramoxine hydrochloride, tricetylammonium chloride, polyquaternium 10, panthenol, panthenol triacetate, vitamin A and derivatives thereof, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, retinol, erthromycin, tretinoin, and mixtures thereof.

18. The composition of claim 16 further comprising, based upon the total weight of the composition, from about 0.001 percent to about 20 percent of the benefit agent.

19. The composition of claim 16 further comprising a suspending agent.

20. The composition of claim 19 wherein the composition is comprised of, based upon the total weight of the composition, from about 0.01 percent to about 5 percent of the suspending agent.

21. The composition of claim 19 wherein the suspending agent is selected from the group consisting of carbomer, hydroxyethyl cellulose, methylvinylether/maleic anhydride copolymer crosslinked with 1,9-decadiene PolyVM/MA (PVM/MA decadiene crosspolymer), Acrylates/Aminoacrylates C10–30 Alkyl PEG-20 Itaconate Copolymer, and mixtures thereof.

22. The composition of claim 1 or claim 2, in the form of a shampoo, a gel, a bath, a cream, a lotion, or a mousse.

23. A method of cleansing the skin, hair and/or nails, comprising the step of:
applying an effective amount of the composition according to claim 1 or claim 2.

24. The composition according to claim 1 or claim 2 wherein:
(i) said crosslinked water soluble polymer is mercaptol propyl copolymer; and
(ii) said polypeptide is a polysarcosine.

* * * * *